United States Patent
Arai et al.

(10) Patent No.: US 6,600,053 B2
(45) Date of Patent: Jul. 29, 2003

(54) METHOD OF PREPARING PHOTOSENSITIVE RESIN COMPOSITION

(75) Inventors: Noriyoshi Arai, Hitachi (JP); Makoto Kaji, Hitachi (JP); Akihiro Sasaki, Hitachi (JP); Toshiki Hagiwara, Sagamihara (JP)

(73) Assignees: Hitachi Chemical DuPont Microsystems Ltd., Tokyo (JP); Hitachi Chemical DuPont Microsystems L.L.C., Wilmington, DE (US)

( * ) Notice: Subject to any disclaimer, the term of this patent is extended or adjusted under 35 U.S.C. 154(b) by 0 days.

(21) Appl. No.: 09/941,703

(22) Filed: Aug. 30, 2001

(65) Prior Publication Data

US 2002/0037991 A1 Mar. 28, 2002

Related U.S. Application Data

(62) Division of application No. 09/431,773, filed on Nov. 1, 1999, now Pat. No. 6,329,494.

(30) Foreign Application Priority Data

Oct. 30, 1998 (JP) ............................ 10-310522
Nov. 30, 1998 (JP) ............................ 10-339480
Jan. 27, 1999 (JP) ............................ 11-18393

(51) Int. Cl.$^7$ ..................... C07D 407/02; C07D 307/77
(52) U.S. Cl. ........................ 549/241; 549/240
(58) Field of Search ............... 560/76; 562/488; 549/241, 240

(56) References Cited

U.S. PATENT DOCUMENTS

| | | | |
|---|---|---|---|
| 4,499,149 A | 2/1985 | Berger | |
| 5,077,415 A | * 12/1991 | Jasne et al. | 549/242 |
| 5,395,918 A | 3/1995 | Harris et al. | |
| 5,480,964 A | 1/1996 | Harris et al. | |
| 5,814,894 A | 9/1998 | Igarashi et al. | |

FOREIGN PATENT DOCUMENTS

JP 05-112641 A 5/1993
JP 05-171018 A 7/1993

OTHER PUBLICATIONS

Polymer (1999), 40(18), 4987–5002, XP–004164966; "Dianhydride architectural effects on the relaxation behaviors and thermal and optical properties of organo–soluble aromatic polyimide films", Li et al.

Polymer Engineering and Science, Mar. 1999, vol. 39, No. 3, 586–593, XP–002166179, "Laser Light–Scattering Studies of Soluble High Performance Fluorine–Containing Polyimides", Kwan et al.

Macromolecules, 1998, 31, 2080–2086, XP–002166180, "Organo–Soluble Polyimides: Synthesis and Polymerization of 2,2'–Bis (trifluoromethyl)–4,4',5,5'–Biphenyltetracarboxylic Diahydride", Lin et al.

* cited by examiner

Primary Examiner—Charanjit S. Aulakh
(74) Attorney, Agent, or Firm—Griffin & Szipl, P.C.

(57) ABSTRACT

A 6,6'-dialkyl-3,3',4,4'-biphenyltetracarboxylic dianhydride is prepared by brominating a 4-alkylphthalic anhydride at its 5-position, and coupling the bromination product in the presence of a nickel catalyst; A photosensitive resin composition containing a polyimide precursor having repetitive units of general formula (7) is applied onto a substrate, exposed to i-line, developed and heated to form a polyimide relief pattern.

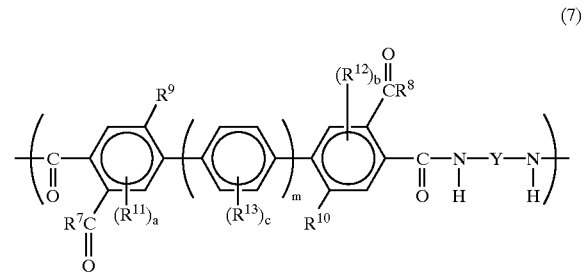

(7)

wherein Y is a divalent organic group, $R^7$ and $R^8$ are OH or a monovalent organic group, $R^9$ and $R^{10}$ are a monovalent hydrocarbon group, $R^{11}$, $R^{12}$ and $R^{13}$ are a monovalent hydrocarbon group, a and b are an integer of 0 to 2, c is an integer of 0 to 4, and m is an integer of 0 to 3.

2 Claims, 4 Drawing Sheets

METHOD OF PREPARING PHOTOSENSITIVE RESIN COMPOSITION

This application is a division of U.S. Patent Application Ser. No. 09/431,773, filed Nov. 1, 1999, now U.S. Pat. No. 6,329,494 B1, which application is related to and claims the early filing date of Japanese Patent Application No. 10-310522, filed Oct. 30, 1998; Japanese Patent Application No. 10-339480, filed Nov. 30, 1998; and Japanese Patent Application No. 11-18393, filed Jan. 27, 1999. The entire disclosures of the above applications and U.S. Patent are hereby incorporated by reference.

BACKGROUND OF THE INVENTION (a) Field of the Invention

The invention relates to a novel tetracarboxylic dianhydride and its derivatives and production. Particularly, it relates to a tetracarboxylic dianhydride useful for producing polyimide precursors or polyimides having low thermal expansion and low residual stress and being suitable for preparing photosensitive resin compositions, and relates to the production and derivatives thereof. The polyimide precursors afford the photosensitive resin compositions with good i-line transmissivity, high-speed developability, high resolution and good dimensional accuracy to suit them to the production of interlayer insulating films or surface-protecting films in semiconductor devices.

It also relates to a polyimide precursor and a polyimide with good heat resistance and good i-line transparency, to a resin composition which contains them and is useful for electronic parts such as semiconductor devices or multilayer wiring boards, and to electronic parts.

It also relates to a photosensitive resin composition and its use for forming relief patterns, and to electronic parts. It particularly relates to a negative or positive, photosensitive resin composition, its use for forming relief patterns and electronic parts using it, which has good i-line transmissivity and, on heating, is capable of being into a heat-resistant polyimide polymer suitable for surface-protecting films, interlayer insulating films and others for electronic parts such as semiconductor devices.

(b) Description of the Related Art

A recent tendency in semiconductor industries has been to replace conventional inorganic interlayer insulating materials with highly heat-resistant organic materials such as polyimide resins because of the characteristic advantages that such organic materials offer.

Circuit patterning on semiconductor integrated circuits or printed boards needs various complicated steps, including coating substrate surfaces with resists, exposing predetermined areas, removing unnecessary parts by etching or the like and washing the substrate surfaces. This has raised a desire to new heat-resistant photosensitive materials which can remain as insulating materials on desired areas after formed into patterned resists by exposure and development.

For example, there have been proposed heat-resistant photosensitive materials containing photosensitive polyimides or cyclized polybutadienes as base polymers, and photosensitive polyimides are particularly noted for their good heat-resistance and easy removal of impurities.

The first-proposed photosensitive polyimides comprise a polyimide precursor and a dichromate (Japanese Patent Application Examined Publication No. 49-17374). In spite of their practical photosensitivity and good film formability, they have found no practical use due to poor storage stability and the residual chromium ion in the product polyimides.

It has been proposed to evade these drawbacks by, for example, mixing polyimide precursors with compounds having photosensitive groups (Japanese Patent Application Unexamined Publication No. 54-109828), or by introducing photosensitive groups into polyimide precursors through the reaction of the functional groups of the polyimide precursors with the functional groups of compounds having the photosensitive groups (Japanese Patent Application Unexamined Publication Nos. 56-24343 and 60-100143).

Such photosensitive polyimide precursors, however, suffer from low sensitivity and defective patterns. This is attributable to the main skeleton derived from aromatic monomers, which contributes good heat-resistance and excellent mechanical properties but makes the polyimide precursors themselves absorb light, thereby lowering the transparency to ultraviolet light and hindering effective photochemical reactions in the exposed areas.

In addition, today's high integration on semiconductors requires increasing preciseness in fabrication rule and higher resolution.

To meet these needs, the conventional contact/proximity aligners using parallel light are being replaced by 1:1 projection aligners called mirror projectors, and further by reduction projection aligners called steppers.

Steppers use a monochromatic light, such as a high-power frequency light of ultra-high-pressure mercury-vapor lamps or an excimer laser. Most of the conventional steppers are g-line steppers using a visible light (435 nm wavelength) of ultra-high-pressure mercury vapor lamps, which is called g-line. The increasing preciseness of fabrication rule, however, needs steppers using light of shorter wavelengths, and i-line steppers (wavelength: 365 nm) are taking the place of g-line steppers (wavelength: 435 nm).

Nevertheless, for the above-mentioned reasons, conventional photosensitive polyimide-based polymers designed for contact/proximity aligners, mirror projection aligners and g-line steppers have poor transparency, particularly almost no transparency to I-line (wavelength: 365 nm), and cannot form desired patterns with I-line steppers.

LOC (Lead On Chip system), which is a high-density semiconductor packaging system, needs thicker surface-protecting polyimide films. The thicker the films, the deeper the problem of poor transparency. Therefore, there is a strong desire for photosensitive polyimides which have a high i-line percent transmittance and form polyimide patterns of good profile by exposure with i-line steppers.

On the other hand, as the diameter of silicon wafers to be substrates has increased with the years, there has arisen the problem of larger warp of silicon wafers coated with surface-protecting polyimide films due to the difference between polyimides and silicon wafers in thermal expansion coefficient. This raised another strong desire for photosensitive polyimides which are much less thermally expansive than conventional polyimides. Rigidly structured molecules generally contribute to decreasing the thermal expansion, but aggravate photosensitivity due to their little transparency to i-line. Flexibly structured molecules decrease the stress applied to silicon wafers to decrease warp and can transmit i-line, but cannot afford the good heat-resistance required of polyimide surface-protecting films.

To improve the i-line transmissivity, it has been proposed to introduce fluorine into polyimides (Japanese Patent Application Unexamined Publication No. 8-234433) or to bend the molecule chains of polyimides (Japanese Patent Application Unexamined Publication No. 8-36264). Nevertheless, fluorine-containing polyimides are less adhesive to silicon wafers, and aggravate the reliability of semiconductor elements. The polyimides having bent molecule chains have poor heat-resistance and high thermal expansion coefficient due to the weak mutual interaction of molecules, and aggravate the reliability of semiconductor elements.

SUMMARY OF THE INVENTION

An object of this invention is to provide a novel tetracarboxylic dianhydride, a novel tetracarboxylic acid, its derivatives and a method of producing it. They are useful as raw materials for polyimide precursors which have not only a rigid structure ensuring low thermal expansion and good heat-resistance but also an i-line transmissivity enough for practical applications.

This invention provides a 6,6'-dialkyl-3,3',4,4'-biphenyltetracarboxylic dianhydride represented by general formula (1):

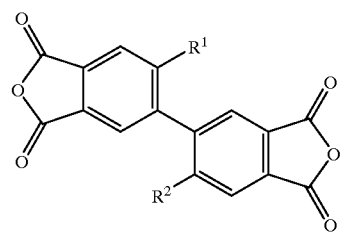

(1)

wherein $R^1$ and $R^2$ each independently represent an alkyl group.

In one embodiment of the invention, the $R^1$ and $R^2$ in the general formula (1) are methyl groups.

This invention further provides a 6,6'-dialkyl-3,3',4,4'-biphenyltetracarboxylic acid or a derivative thereof, which is represented by general formula (2):

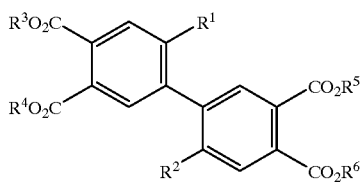

(2)

wherein $R^1$ and $R^2$ each independently are an alkyl group, $R^3$, $R^4$, $R^5$ and $R^6$ each independently are a hydrogen atom, an alkyl group, an alkali metal ion or an ammonium ion.

This invention further provides a method of preparing a 6,6'-dialkyl-3,3',4,4'-biphenyltetracarboxylic dianhydride, comprising brominating a 4-alkylphthalic anhydride at its 5-position, and then coupling the bromination product in the presence of a nickel catalyst.

In one embodiment of the invention, the method comprises heating a water suspension of a 4-alkylphthalic anhydride and a bromate and adding thereto concentrated sulfuric acid to form a 4-alkyl-5-bromophthalic acid, esterifying the 4-alkyl-5-bromophthalic acid to form a 4-alkyl-5-bromophthalic diester, coupling the 4-alkyl-5-bromophthalic diester in the presence of a nickel catalyst to form a 6,6'-dialkyl-3,3',4,4'-biphenyltetracarboxylic tetraester, hydrolyzing the 6,6'-dialkyl-3,3',4,4'-biphenyltetracarboxylic tetraester to form a 6,6'-dialkyl-3,3',4,4'-biphenyltetracarboxylic acid, and dehydrating the 6,6'-dialkyl-3,3',4,4'-biphenyltetracarboxylic acid into a 6,6'-dialkyl-3,3',4,4'-biphenyltetracarboxylic dianhydride.

Another object of this invention is to provide a polyimide precursor which has good 1-line transmissivity in spite of their rigid structures and, after imidation, exhibits good heat-resistance. The invention also provides a polyimide derived from the polyimide precursor.

That is, this invention provides a polyimide precursor having repetitive units represented by general formula (7):

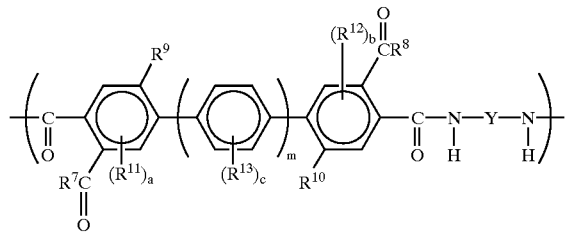

(7)

wherein Y is a divalent organic group, $R^7$ and $R^8$ each independently are OH or a monovalent organic group, $R^9$ and $R^{10}$ each independently are a monovalent hydrocarbon group, $R^{11}$, $R^{12}$ and $R^{13}$ each independently are a monovalent hydrocarbon group, a and b each independently are an integer of 0 to 2, c is an integer of 0 to 4, and m is an integer of 0 to 3.

Herein, every repetitive unit of the polyimide precursor may have any one of three structures including the structure of formula (7), which are structurally isomeric with one another. The two structures other than that of the general formula (7) are represented by the following general formulae (7') and (7"):

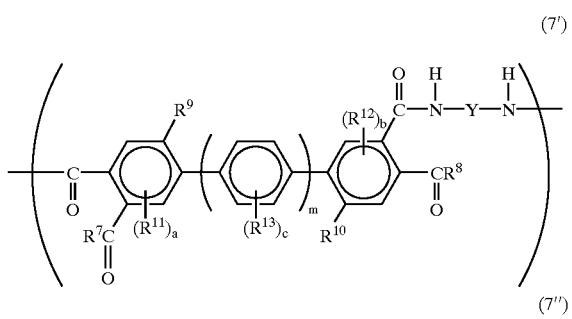

(7')

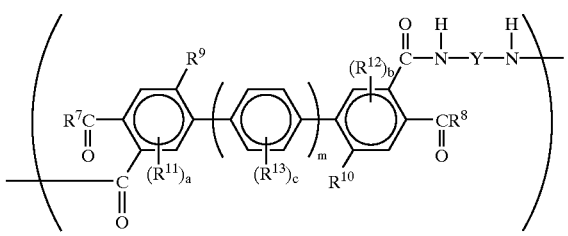

(7")

In one embodiment of the invention, the polyimide precursor has repetitive units represented by general formula (8):

(8)

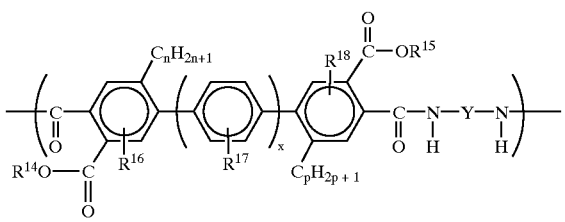

wherein Y is a divalent organic group, $R^{14}$, $R^{15}$, $R^{16}$, $R^{17}$ and $R^{18}$ each independently are a hydrogen atom or an alkyl group, x is 0 or 1, n and p each independently are an integer of 1 to 10.

In one embodiment of the invention, the polyimide precursor has repetitive units of general formula (8) wherein $R^{14}$, $R^{15}$, $R^{16}$ and $R^{18}$ are hydrogen atoms, and x is 0.

In one embodiment of the invention, n and p in general formula (8) are 1.

Another object of the invention is to provide a polyimide precursor suitable for photosensitive resin compositions.

That is, in one embodiment of the invention, the polyimide precursor has repetitive units of general formula (9):

(9)

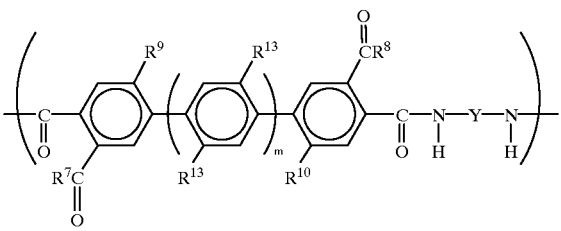

wherein Y, $R^7$, $R^8$, $R^9$, $R^{10}$, $R^{13}$ and m are as defined above.

In one embodiment, the divalent organic group represented by Y in the general formula (9) is represented by general formula (10):

(10)

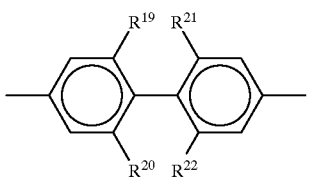

wherein $R^{19}$, $R^{20}$, $R^{21}$ and $R^{22}$ each independently are a hydrogen atom, an alkyl group, a fluorine atom or a fluoroalkyl group, with the proviso that two or more of them are alkyl groups, fluorine atoms or fluoroalkyl groups.

To be suited for negative, photosensitive resin compositions, the polyimide precursor preferably has repetitive units of the general formula (9) wherein at least one of $R^7$ and $R^8$ is a monovalent organic group having a carbon—carbon unsaturated double bond.

To be suited for positive, photosensitive resin compositions, the polyimide precursor preferably has repetitive units of the general formula (9) wherein Y is a divalent organic group having a carboxyl group or a phenolic hydroxyl group. Still preferably, in general formula (9), $R^7$ and $R^8$ are hydroxyl groups.

Another object of this invention is to provide a polyimide which has good i-line transmissivity in spite of its rigid structure and exhibits excellent heat-resistance.

That is, this invention provides a polyimide having repetitive units represented by general formula (11):

(11)

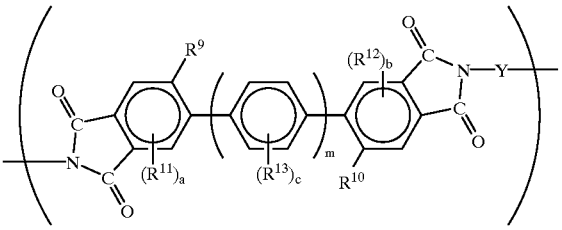

wherein Y is a divalent organic group, $R^9$ and $R^{10}$ each independently are a monovalent hydrocarbon group, $R^{11}$, $R^{12}$ and $R^{13}$ each independently are a monovalent hydrocarbon group, a and b each independently are an integer of 0 to 2, c is an integer of 0 to 4, and m is an integer of 0 to 3.

In one embodiment of the invention, the polyimide has repetitive units represented by general formula (12):

(12)

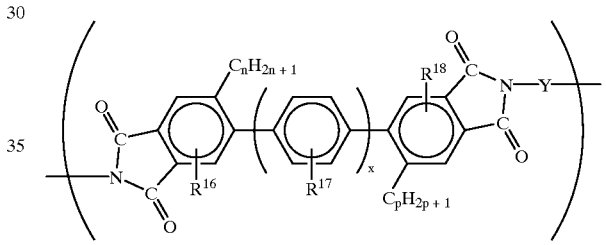

wherein Y is a divalent organic group, $R^{16}$, $R^{17}$ and $R^{18}$ each independently are a hydrogen atom or an alkyl group, x is 0 or 1, n and p each independently are an integer of 1 to 10; and in cases $R^{16}$, $R^{17}$ and $R^{18}$ are alkyl groups, one or a plurality of each of $R^{16}$, $R^{17}$ and $R^{18}$ may be bonded to the benzene rings on any positions.

In one embodiment of the invention, the polyimide has repetitive units represented by the general formula (12) wherein $R^{16}$ and $R^{18}$ are hydrogen atoms, and x is 0.

In one embodiment of the invention, n and p in the general formula (12) are 1.

Another object of this invention is to provide a resin composition which contains a polyimide or its precursor having good i-line transparency in spite of its rigid structure, and, after imidation, exhibits excellent heat-resistance. It is suitable for forming surface-protecting films or interlayer insulating films in semiconductor devices, or interlayer insulating films in multilayer wiring boards.

That is, the invention provides a resin composition containing the polyimide precursor having repetitive units of the general formula (7) or the polyimide having repetitive units of the general formula (11).

In one embodiment of the invention, the resin composition contains the polyimide precursor having the repetitive units represented by the general formula (8):

(8)

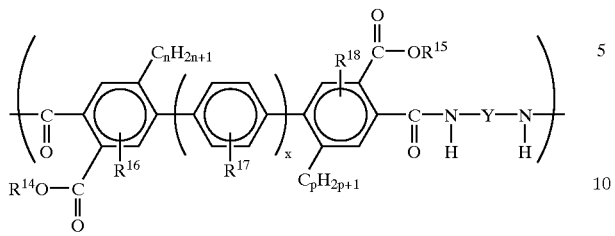

(9)

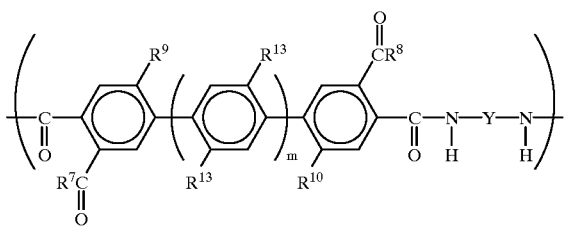

wherein Y is a divalent organic group, $R^{14}$, $R^{15}$, $R^{16}$, $R^{17}$ and $R^{18}$ each independently are a hydrogen atom or an alkyl group, x is 0 or 1, and n and p each independently are an integer of 1 to 10;

or the polyimide having the repetitive units represented by the general formula (12):

(12)

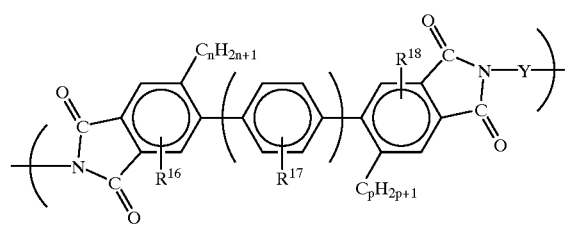

wherein Y is a divalent organic group, $R^{16}$, $R^{17}$ and $R^{18}$ each independently are a hydrogen atom or an alkyl group, x is 0 or 1, and n and p each independently are an integer of 1 to 10.

Another object of the invention is to provide an extremely reliable electronic part, which has a surface-protecting or interlayer insulating film formed from a material having good i-line transmissivity in spite of its rigid structure and exhibiting good heat-resistance after imidation.

That is, the invention provides an electronic part (hereinafter, it may be called "electronic part (a)" sometimes) which has a film of the polyimide having the repetitive units of the general formula (11), preferably the general formula (12).

Another object of the invention is to provide a photosensitive resin composition having good i-line transmissivity and high resolution.

That is, the invention provides a photosensitive resin composition which contains the polyimide precursor having the repetitive units represented by the general formula (7).

In one embodiment of the invention, the photosensitive resin composition contains a polyimide precursor having repetitive units represented by general formula (9):

wherein Y, $R^7$, $R^8$, $R^9$, $R^{10}$, $R^{13}$ and m are as defined above.

In one embodiment of the invention, the photosensitive resin composition contains a polyimide precursor having repetitive units of the general formula (9) wherein the divalent organic group Y is represented by general formula (10):

(10)

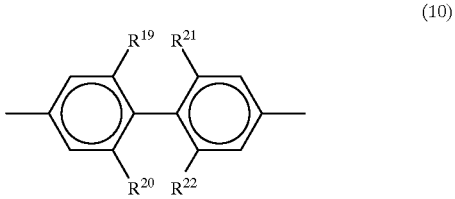

wherein $R^{19}$, $R^{20}$, $R^{21}$ and $R^{22}$ are as defined above.

Another object of the invention is to provide a photosensitive resin composition which has the above-mentioned good properties and is suited to negative patterning.

That is, in one embodiment of the invention, the photosensitive resin composition has repetitive units of the general formula (9) wherein at least one of $R^7$ and $R^8$ is a monovalent organic group having a carbon—carbon unsaturated double bond.

Preferably, the photosensitive resin composition further contains a photopolymerization initiator.

Another object of the invention is to provide a photosensitive resin composition which has the above-mentioned good properties and is suited to positive patterning using an aqueous alkali solution for development.

That is, in another embodiment of the invention, the photosensitive resin composition has repetitive units of the general formula (9) wherein Y is a divalent organic group having a carboxyl group or a phenolic hydroxyl group or wherein $R^7$ and $R^8$ are hydroxyl groups, and further contains a compound capable of generating an acid when exposed to light.

In one embodiment of the invention, the compound capable of generating an acid when exposed to light is an o-quinonediazide compound.

Another object of the invention is to provide a method of forming relief patterns with high resolution by exposure using i-line.

That is, the present invention provides a method of forming a relief pattern, comprising a step of applying the photosensitive resin composition of the invention onto a substrate and drying it thereon, a step of exposing it, a step of developing it, and a step of heating it.

In one embodiment of the invention, the exposure is conducted by using i-line as a light for the exposure.

Another object of the invention is to provide an extremely reliable electronic part which has a surface-protecting or interlayer insulating film having a relief pattern of high resolution.

That is, the invention provides an electronic part (hereinafter, it may be called "electronic part (b)" sometimes) containing a layer of the relief pattern formed by the method mentioned above.

In one embodiment of the invention, the layer of the relief pattern is a surface-protecting film or a interlayer insulating film.

Figure 1:
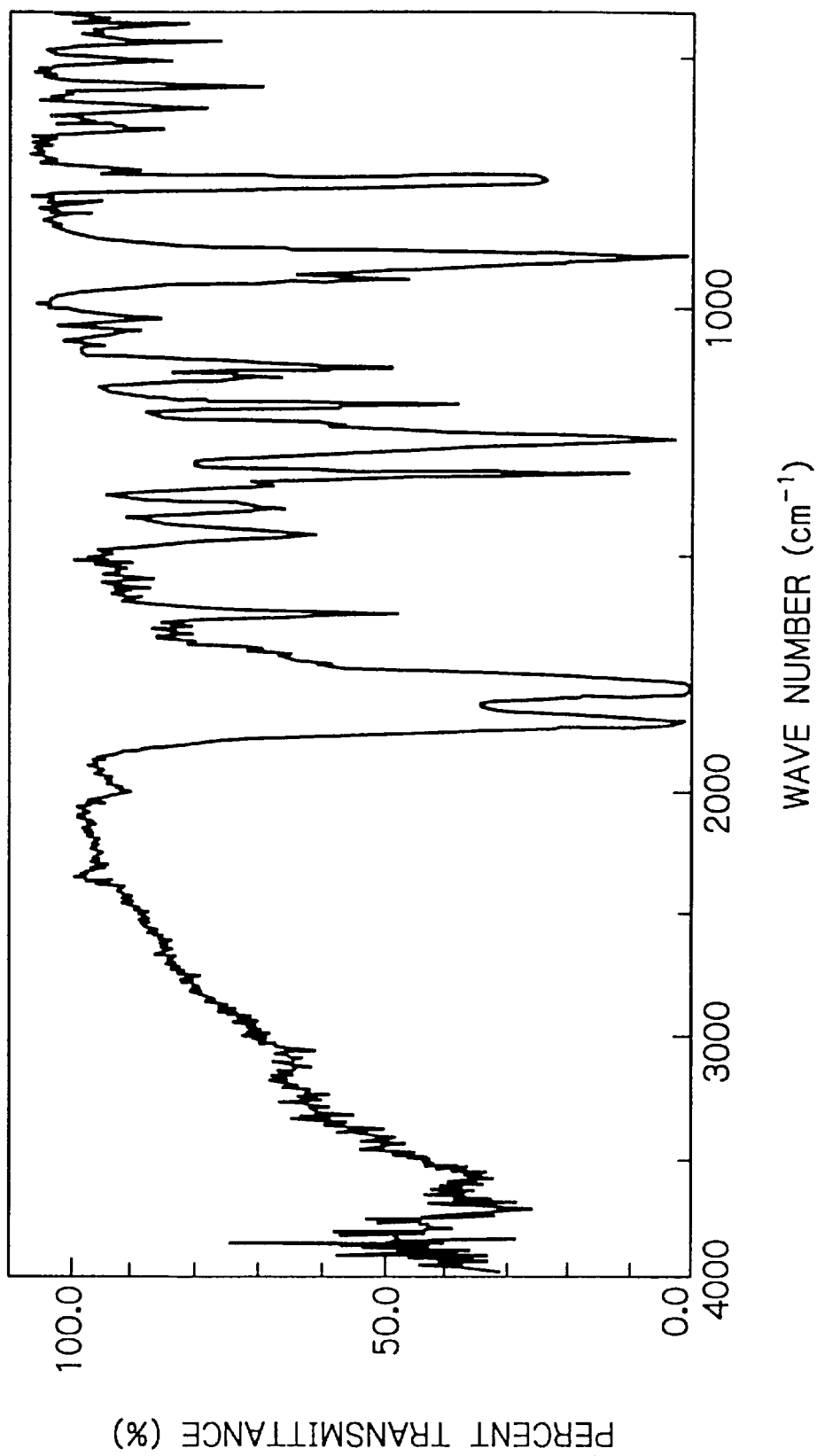
FIG. 1 is a diagram showing an IR spectrum of a typical tetracarboxylic dianhydride according to the invention.

DESCRIPTION OF THE PREFERRED EMBODIMENTS (A) Tetracarboxylic Dianhydrides, Tetracarboxylic Acids, and Derivatives and Production thereof In the 6,6'-dialkyl-3,3',4,4'-biphenyltetracarboxylic dianhydride of the invention represented by general formula (1), examples of the alkyl group for $R^1$ and $R^2$ include alkyls of 1 to 4 carbon atoms, such as methyl, ethyl, n-propyl, isopropyl, n-butyl, sec-butyl or tert-butyl.

By the alkyl groups $R^1$ and $R^2$, the two aromatic rings of the biphenyl are staggered and as well relieved from the electron deficient state.

The 6,6'-dialkyl-3,3',4,4'-biphenyltetracarboxylic dianhydride of the invention is obtainable by the method of the invention, comprising brominating a 4-alkylphthalic anhydride at its 5-position, and then coupling the bromination product in the presence of a nickel catalyst.

The 6,6'-dialkyl-3,3',4,4'-biphenyltetracarboxylic dianhydride may be produced either from one brominated 4-alkylphthalic anhydride or from two brominated 4-alkylphthalic anhydrides having different alkyl groups.

The selective bromination of a 4-alkylphthalic anhydride at its 5 position can be performed, for example, by heating a water suspension of a 4-alkylphthalic anhydride and a bromate, and adding thereto concentrated sulfuric acid. By this reaction, 4-alkyl-5-bromophthalic acid is formed. The 4-alkyl-5-bromophthalic acid is esterified into a 4-alkyl-5-bromophthalic diester to protect the carboxylic acid moiety with two carboxyl-protecting groups. The 4-alkyl-5-bromophthalic diester is coupled in the presence of a nickel catalyst to form a 6,6'-dialkyl-3,3',4,4'-biphenyltetracarboxylic tetraester. Then the 6,6'-dialkyl-3,3',4,4'-biphenyltetracarboxylic tetraester is hydrolyzed to cleave the four carboxyl-protecting groups. The resulting 6,6'-dialkyl-3,3',4,4'-biphenyltetracarboxylic acid is dehydrated to form the objective 6,6'-dialkyl-3,3',4,4'-biphenyltetracarboxylic dianhydride.

For example, the selective bromination at the 5-position can be achieved preferably by heating a water suspension of a 4-alkylphthalic anhydride and a bromate such as potassium bromate, sodium bromate or ammonium bromate at 70 to 120° C., preferably 90 to 100° C., and adding dropwise concentrated sulfuric acid thereto gradually. Thus, a dicarboxylic acid of the general formula (3) is obtained:

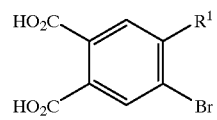

(3)

wherein $R^1$ as defined above for the general formula (1).

The crude product may be used in the next reaction as such, or may be recrystallized from water in the presence of powdery active carbon or the like to obtain a pure sample. The dicarboxylic acid is heated to reflux in the presence of an excess halogenating agent such as thionyl chloride, oxalyl chloride, phosphorus chloride or thionyl bromide to form an acyl halide. An alkyl alcohol of 1 to 5 carbon atoms is then added thereto and the mixture is heated to reflux to form a dialkyl ester, such as a dimethyl ester of general formula (4):

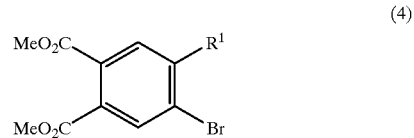

(4)

wherein $R^1$ is as defined above for the general formula (1). Alternatively, the dimethyl ester is obtainable by heating the dicarboxylic acid of the general formula (3) and an alkyl alcohol, such as methanol, to reflux in the presence of an acid catalyst, such as sulfuric acid, and then adding toluene thereto to remove water as a toluene azeotrope.

The dialkyl ester is coupled using a nickel catalyst such as nickel dichloride, preferably in the presence of a phosphine, such as triphenylphosphine, trifurylphosphine or tritolylphosphine, bipyridine and a reducing agent, such as zinc dust, aluminum powder, tin powder or manganese powder, in an aprotic polar solvent, such as N,N-dimethylformamide (DMF), N,N-dimethylacetamide (DMAc) or hexamethylphosphortriamide (HMPA). The amount of the nickel catalyst is generally 2 to 10 mol %, preferably 3 to 5 mol % based on the dialkyl ester. The amount of bipyridine is generally 0.5 to 1.5 mol, preferably 0.9 to 1.1 mol per mol of the nickel catalyst. The amount of the reducing agent is generally at least triple the molar quantity of the nickel catalyst, more preferably 20 to 50 moles per mol of the nickel catalyst. The reaction temperature is generally 70 to 120° C., and the reaction time is generally 4 to 10 hours. Thus a tetraester, such as a tetramethyl 6,6'-dialkyl-3,3',4,4'-biphenyltetracarboxylate of the general formula (5):

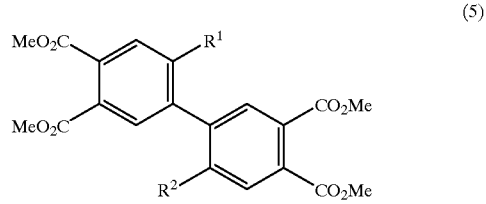

(5)

wherein $R^1$ and $R^2$ are as defined above; is obtained.

Because of the ester bonds in the molecule, any coupling process via a Grignard agent can never be applicable. The Ullmann's coupling using a copper catalyst, although known to be applicable for compounds having ester moieties, does not proceed at all in this case.

The tetraester thus obtained is a kind of the tetracarboxylic acid derivative of the general formula (2). The tetraester is readily hydrolyzed by heating it to reflux in the presence of an aqueous solution of 2 to 8 M, preferably 2 to 4 M sodium hydroxide or the like to form a 6,6'-dialkyl-3,3',4,4'-biphenyltetracarboxylic acid of general formula (6):

(6)

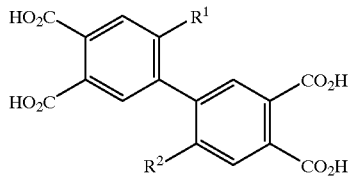

wherein $R^1$ and $R^2$ are as defined above. The tetracarboxylic acid is also a kind of the derivative represented by the general formula (2).

On heating the tetracarboxylic acid in vacuo, preferably at 1 to 5 mmHg, at 150 to 180° C. for 4 to 6 hours, intermolecular dehydration condensation occurs, to give the acid anhydride of the general formula (1).

The tetracarboxylic acid or its derivative of the general formula (2) is also useful as a material for various polyimide precursors.

In the general formula (2), $R^3$, $R^4$, $R^5$ and $R^6$ each independently are a hydrogen atom, an alkyl group, an alkali metal ion or an ammonium ion; and examples of the alkyl group include alkyl groups of 1 to 4 carbon atoms, such as methyl, ethyl, n-propyl, isopropyl, n-butyl, sec-butyl or tert-butyl; examples of the alkali metal ion include sodium, potassium or lithium.

Among the compounds of general formula (2), those wherein $R^3$, $R^4$, $R^5$ and $R^6$ are alkali metal ions are obtainable by a stoichiometric reaction of the tetracarboxylic acid of the general formula (6) produced as above with a base such as sodium hydroxide.

For example, the tetracarboxylic dianhydride of the invention is suited to the production of the polyimide precursor of the invention.

(B) Polyimide Precursors

The polyimide precursor of the present invention is a polymer having repetitive units of the general formula (7). Having the repetitive units of the general formula (7), the polyimide precursor itself has good transparency, and after imidation, has a good heat-resistance which the conventional polyimide precursors of the same transparency cannot offer.

The percentage of the repetitive units of the general formula (7) in all repetitive units is not limited, but preferably such that the polyimide precursor has the desired i-line (365 nm) percent transmittance and, after imidation, the desired heat-resistance. It is preferably 10 to 100 mol % based on all repetitive units.

The polyimide precursor, generally, may be produced by using as raw materials a tetracarboxylic dianhydride of the general formula (13):

(13)

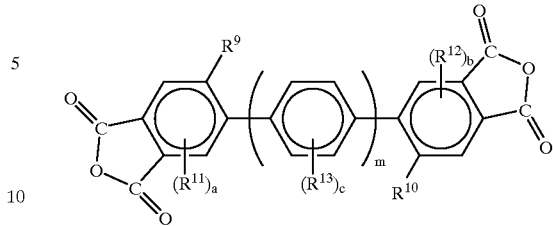

wherein $R^9$, $R^{10}$, $R^{12}$, $R^{13}$, a, b, c and m are as defined above; or its derivative, a diamine giving the structure Y and other optional compounds for introduction of side chains.

Examples of the monovalent hydrocarbon groups for $R^9$, $R^{10}$ $R^{11}$, $R^{12}$ and $R^{13}$ include alkyl groups, such as methyl, ethyl or propyl, and aryl groups, such as phenyl, preferably those of 1 to 10 carbon atoms, more preferably alkyl groups of 1 to 10 carbon atoms, particularly preferably alkyl groups of 1 to 4 carbon atoms.

Among all, tetracarboxylic dianhydrides of the general formula (14):

(14)

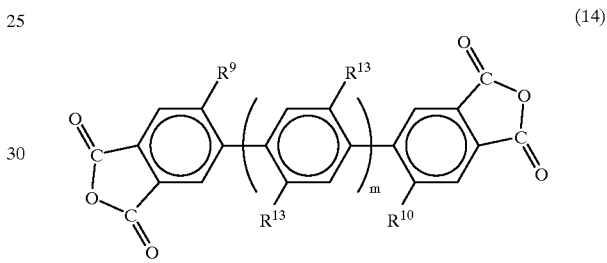

wherein $R^9$, $R^{10}$, $R^{13}$ and m are as defined above;
are suitable for the preparation of polyimide precursors to be used as a material for photosensitive resin compositions.

Preferred examples of the tetracarboxylic dianhydrides with such structures include 6,6'-dialkyl-3,3',4,4'-biphenyltetracarboxylic dianhydrides, namely the tetracarboxylic dianhydrides according to this invention, such as 6,6'-dimethyl-3,3',4,4'-biphenyltetracarboxylic dianhydride, 6,6'-diethyl-3,3',4,4'-biphenyltetracarboxylic dianhydride, 6,6'-dipropyl-3,3',4,4'-biphenyltetracarboxylic dianhydride, 6,6'-diisopropyl-3,3',4,4'-biphenyltetracarboxylic dianhydride, 6,6'-dibutyl-3,3',4,4'-biphenyltetracarboxylic dianhydride and 6,6'-di-tert-butyl-3,3',4,4'-biphenyltetracarboxylic dianhydride.

The 6,6'-dialkyl-3,3',4,4'-biphenyltetracarboxylic dianhydrides are obtainable by brominating a 4-alkylphthalic anhydride at 5-position, and coupling the bromination product in the presence of a nickel catalyst.

The tetracarboxylic dianhydride of the general formula (13) or its derivative is essential for the production of the polyimide precursor of the invention, and other carboxylic dianhydrides or their derivatives may also be used together in such amounts as not to aggravate the i-line transmissivity and heat-resistance.

The optional tetracarboxylic dianhydrides are not particularly limited, and examples include aromatic tetracarboxylic dianhydrides, such as oxydiphthalic dianhydrides (such as 3,3',4,4'-diphenyl ether-tetracarboxylic dianhydride), pyromellitic dianhydride, 3,3',4,4'-benzophenonetetracarboxylic dianhydride, 3,3',4,4'-biphenyltetracarboxylic dianhydride, 2,3,3',4'-biphenyltetracarboxylic dianhydride, 2,2',3,3'- biphenyltetracarboxylic dianhydride, 1,2,5,6-naphthalenetetracarboxylic dianhydride, 2,3,6,7-naphthalenetetracarboxylic dianhydride, 1,4,5,8-naphthalenetetracarboxylic dianhydride, 2,3,5,6-pyridinetetracarboxylic dianhydride, 3,4,9,10-perylenetetracarboxylic dianhydride, sulfonyldiphthalic dianhydrides (such as 3,3',4,4'-diphenyl sulfone-tetracarboxylic dianhydride), m-terphenyl-3,3',4,4'-tetracarboxylic dianhydride, p-terphenyl-3,3'-4,4'-tetracarboxylic dianhydride, 1,1,1,3,3,3-hexafluoro-2,2-bis (2,3- or 3,4-dicarboxyphenyl)propane dianhydride, 2,2-bis (2,3- or 3,4-dicarboxyphenyl)propane dianhydride, 2,2-bis{4'-(2,3- or 3,4-dicarboxyphenoxy)phenyl}propane dianhydride, 1,1,1,3,3,3-hexafluoro-2,2-bis{4'-(2,3- or 3,4-dicarboxyphenoxy)phenyl}propane dianhydride and tetracarboxylic dianhydrides of general formula (15):

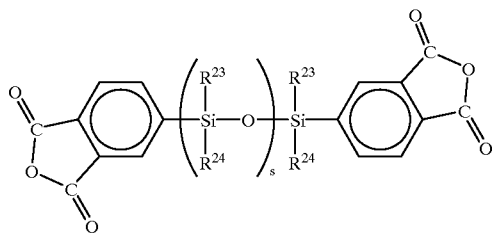

(15)

wherein $R^{23}$ and $R^{24}$ each independently are a monovalent hydrocarbon group, preferably an alkyl group of 1 to 10 carbon atoms or an aryl group of 6 to 12 carbon atoms, plural groups of the same symbol may be identical with or different from one another, s is an integer of at least 1, preferably 1 to 10;

and these may be used individually or in combination of two or more.

Among the optionally additional tetracarboxylic dianhydrides, from the point of i-line transmissivity, the preferred include 3,3',4,4'-biphenyltetracarboxylic dianhydride, 2,3,3',4'-biphenyltetracarboxylic dianhydride, 2,2',3,3'-biphenyltetracarboxylic dianhydride, oxydiphthalic dianhydrides (such as 3,3',4,4'-diphenyl ether-tetracarboxylic dianhydride) and 2,2-bis(3,4-dicarboxyphenyl)hexafluoropropane.

Examples of derivatives of the tetracarboxylic acids include tetracarboxylic acids, tetracarboxylic chlorides, tetracarboxylic monoesters and diesters.

Y in the general formula (7) is a divalent organic group which is typically derived from a diamine reactive to the above-described tetracarboxylic dianhydride or its derivative. In general, the divalent organic group is an aromatic ring such as a benzene ring or naphthalene ring optionally substituted by one or more halogen atoms, hydrocarbon groups, halogenated hydrocarbon groups, hydroxyl groups or carboxyl groups, or an aromatic group comprising 2 to 6 such aromatic rings linked by one or more single bonds, ether groups, sulfone groups, carbonyl groups, thioether groups, methylene groups, alkylidene groups, halogenated alkylidene groups, sulfonyl groups, 9,9-fluorenylidene groups or the like.

Diamines to be used to give such structures are not particularly limited, and examples include 4,4'-(or 3,4'-, 3,3'-, 2,4'- or 2,2'-)diaminodiphenyl ether, 4,4'-(or 3,4'-, 3,3'-, 2,4'- or 2,2'-)diaminodiphenylmethane, 4,4'-(or 3,4'-, 3,3'-, 2,4'- or 2,2'-)diaminodiphenyl sulfone, 4,4'-(or 3,4'-, 3,3'-, 2,4'- or 2,2'-)diaminodiphenyl sulfide, p-phenylenediamine, m-phenylenediamine, p-xylylenediamine, m-xylylenediamine, o-tolidine, o-tolidine sulfone, 4,4'-methylene-bis(2,6-diethylaniline), 4,4'-methylene-bis(2,6-diisopropylaniline), 2,4-diaminomesitylene, 1,5-diaminonaphthalene, 4,4'-benzophenonediamine, bis{4-(4'-aminophenoxy)phenyl}sulfone, 1,1,1,3,3,3-hexafluoro-2,2-bis(4-aminophenyl)propane, 2,2-bis{4-(4'-aminophenoxy)phenyl}propane, 3,3'-dimethyl-4,4'-diaminodiphenylmethane, 3,3',5,5'-tetramethyl-4,4'-diaminodiphenylmethane, bis(4-(3'-aminophenoxy)phenyl} sulfone, 2,2-bis(4-aminophenyl)propane, 9,9-bis(4-aminophenyl)fluorene and 2,2',5,5'-tetrafluoro-4,4'-diaminobiphenyl, and these may be used individually or in combination of two or more.

Among the diamines those impart excellent heat-resistance and high transparency to polyimide precursors are represented by the general formula (16):

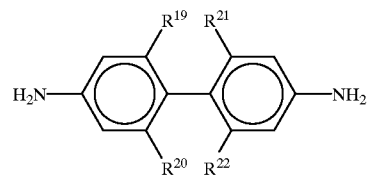

(16)

wherein $R^{19}$, $R^{20}$, $R^{21}$ and $R^{22}$ each independently are an hydrogen atom, an alkyl group, a fluorine atom or a fluoroalkyl group, with the proviso that two or more of them are an alkyl group, a fluorine atom or a fluoroalkyl group. For $R^{19}$, $R^{20}$, $R^{21}$ and $R^{22}$, the preferred alkyl group is of 1 to 5 carbon atoms, such as methyl, ethyl or propyl, the preferred fluoroalkyl is a perfluoroalkyl group of 1 to 5 carbon atoms, such as trifluoromethyl or pentafluoroethyl.

Preferred examples of Y are

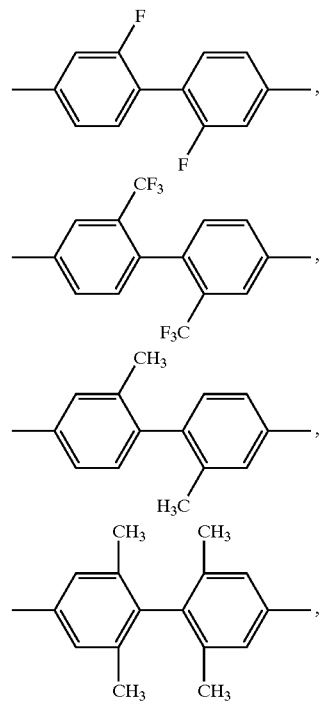

-continued

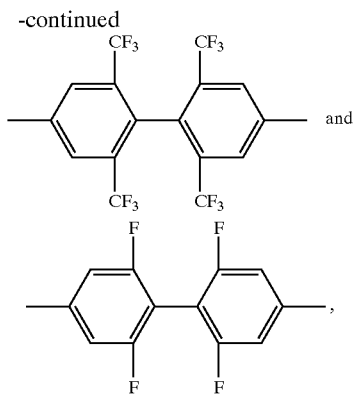

and particularly preferred are

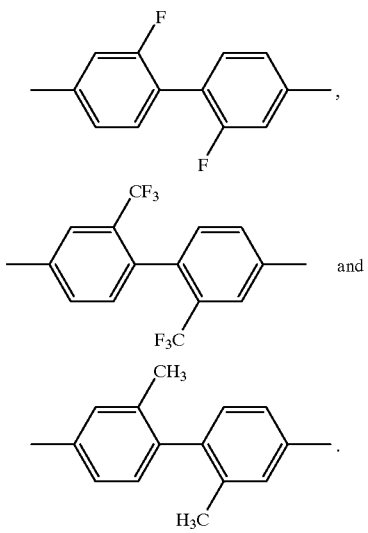

To improve the i-line percent transmittances of the polyimide precursors and the mechanical and thermal properties of polyimide films, the amount of the diamines of the general formula (16) is preferably 10 to 100 mol %, more preferably 50 to 100 mol % of sum total of diamines.

To improve the adhesive property to substrates, aliphatic diamines, such as diaminopolysiloxanes of general formula (17) may optionally be used:

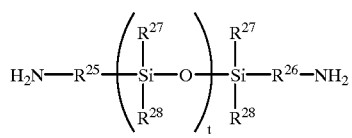

(17)

wherein $R^{25}$ and $R^{26}$ each independently are a divalent hydrocarbon group, for example an alkylene group of 1 to 10 carbon atoms, such as —$(CH_2)_n$—, n being an integer of 1 to 10, $R^{26}$ and $R^{27}$ each independently are a monovalent hydrocarbon group, for example an alkyl group of 1 to 5 carbon atoms, such as a n-alkyl group of 1 to 5 carbon atoms, an alkoxy group of 1 to 5 carbon atoms, such as methoxy, or an aryl group of 6 to 12 carbon atoms, such as phenyl, and t is an integer of 1 or more, preferably 1 to 100.

Among the polyimide precursors of the invention, polyamic acids (that is, those of the general formula (7) or (9) wherein $R^7$ and $R^8$ are hydroxyl groups, or those of the general formula (8) wherein $R^{14}$ and $R^{15}$ are hydrogen atoms) are obtainable by allowing the above-described tetracarboxylic dianhydrides and diamines to undergo ring-opening addition polymerization in an organic solvent. The ratio of the tetracarboxylic dianhydride to the diamine is preferably between 0.7/1 and 1/0.7, as the molar ratio of the former/the latter. Room temperature is enough for the ring-opening addition polymerization, preferably 10 to 40° C., and the reaction time is preferably 6 to 24 hours.

Organic solvents useful for the ring-opening addition polymerization are preferably polar solvents to completely solve the product polyimide precursors, such as N-methyl-2-pyrrolidone, N,N-dimethylacetamide, N,N-dimethylformamide, dimethyl sulfoxide, tetramethylurea, hexamethylphosphortriamide and γ-butyrolactone.

Besides the polar solvents, ketones, esters, lactones, ethers, halogenated hydrocarbons and hydrocarbons may be used, such as acetone, diethyl ketone, methyl ethyl ketone, methyl isobutyl ketone, cyclohexanone, methyl acetate, ethyl acetate, butyl acetate, diethyl oxalate, diethyl malonate, diethyl ether, ethylene glycol dimethyl ether, diethylene glycol dimethyl ether, tetrahydrofuran, dichloromethane, 1,2-dichloroethane, 1,4-dichlorobutane, trichloroethane, chlorobenzene, o-dichlorobenzene, hexane, heptane, octane, benzene, toluene and xylene.

The organic solvents are used individually or in combination of two or more.

Among the polyimide precursors of the invention, polyamidates (namely those of the general formula (7) or (9) wherein at least one of $R^7$ and $R^8$ is an alcohol residue such as alkoxy, or those of the general formula (8) wherein at least one of the $R^{14}$ and $R^{15}$ is an alkyl group) are obtainable by dissolving the above-described diamine and a dehalogenating agent such as pyridine in the above-described organic solvent, adding dropwise a tetracarboxylic acid diester dihalide dissolved in an organic solvent, pouring the reaction product into a bad solvent such as water, and filtering and drying the precipitate. The ratio of sum total of diamines to the tetracarboxylic acid diester dihalide is preferably between 0.6/1 and 1/0.6, more preferably between 0.7/1 and 1/0.7, as the molar ratio of the former/the latter. The reaction temperature is preferably 20 to 40° C., and the reaction time is preferably 1 to 10 hours. The ratio of the dehalogenating agent to the tetracarboxylic acid diester dihalide is preferably between 1.8/1 and 2.2/1, more preferably between 1.9/1 and 2.1/1, as the molar ratio of the former/the latter. The tetracarboxylic acid diester dihalide is obtainable by allowing a tetracarboxylic acid diester, which is produced by the reaction of the tetracarboxylic dianhydride and an alcohol compound, to react with thionyl chloride.

Preferred examples of the alcohol compound are alkyl alcohols of 1 to 6 carbon atoms, such as methanol, ethanol, n-propyl alcohol, isopropyl alcohol, n-butyl alcohol, sec-butyl alcohol, tert-butyl alcohol, isobutyl alcohol, 1-pentanol, 2-pentanol, 3-pentanol, isoamyl alcohol, 1-hexanol, 2-hexanol or 3-hexanol.

The molecular weight of the polyimide precursor of the invention is not particularly limited, and is preferably 20,000 to 100,000 in weight average molecular weight, as measured using an E-type viscometer.

Polyimide Precursors Suitable for Photosensitive Resin Compositions

When the polyimide precursor of the invention is intended for alkali-developable, positive, photosensitive resin compositions or for alkali-developable, negative, photosensitive resin compositions, the polyimide precursor of the invention is made soluble to alkali preferably by the introduction of a divalent organic group having at least one (preferably one to three) phenolic hydroxyl group and/or carboxylic group as the diamine residue for Y in the general formula (7), preferably (9). Examples of diamines providing such a structure include 2,5-diaminobenzoic acid, 3,4-diaminobenzoic acid, 3,5-diaminobenzoic acid, 2,5-diaminoterephthalic acid, bis(4-amino-3-carboxyphenyl) methylene, 4,4'-diamino-3,3'-dicarboxybiphenyl, 4,4'-diamino-5,5'-dicarboxy-2,2'-dimethylbiphenyl, 1,3-diamino-4-hydroxybenzene, 1,3-diamino-5-hydroxybenzene, 3,3'-diamino-4,4'-dihydroxybiphenyl, 4,4'-diamino-3,3'-dihydroxybiphenyl, bis(3-amino-4-hydroxyphenyl) sulfone, bis(4-amino-3-hydroxyphenyl) sulfone, 2,2-bis(3-amino-4-hydroxyphenyl) hexafluoropropane, 2,2-bis(4-amino-3-hydroxyphenyl) hexafluoropropane and bis(4-amino-3-carboxyphenyl) methane.

When this means is used to give an alkali-developable, positive, photosensitive resin compositions or an alkali-developable, negative, photosensitive resin compositions, the amount of diamines for introducing Y of such a structure is preferably 50 to 100 mol % based on sum total of diamines.

Besides the introduction of a divalent organic group having a phenolic hydroxyl group and/or carboxyl group as the diamine residue for Y in the general formula (7), preferably (9), selecting OH for at least one of $R^7$ and $R^8$ also provides photosensitive resin compositions with alkali-developability. To afford alkali-developability by this means, preferably 50 to 100 mol % of the groups $R^7$ and $R^8$ in the polyimide precursor are hydroxyl groups.

To prepare negative, photosensitive resin compositions according to the invention, at least a part, preferably 20 to 100 mol % of the groups $R^7$ and $R^8$ desirably are a monovalent organic groups having a carbon—carbon unsaturated double bond.

Preferred examples of such monovalent organic groups are the following groups which have a carbon—carbon unsaturated double bond introduced through an ionic bond, through an ester bond or through an amide bond:

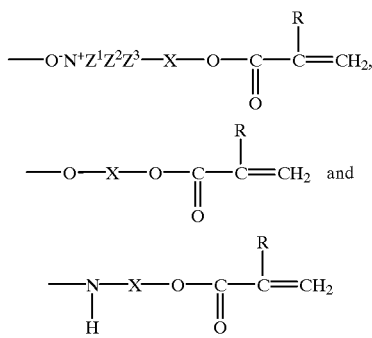

wherein X is a divalent hydrocarbon group, R is a hydrogen atom or methyl, $Z^1$, $Z^2$ and $Z^3$ each independently are a hydrogen atom or a monovalent hydrocarbon group.

Preferred examples of X are alkylene groups of 1 to 10 carbon atoms, and preferred examples of the monovalent hydrocarbon group for $Z^1$, $Z^2$ and $Z^3$ are alkyl groups of 1 to 5 carbon atoms.

The introduction of a carbon—carbon unsaturated double bond through an ionic bond is preferably achieved using a derivative of acrylic acid or methacrylic acid having an amino group (acrylic compounds having an amino group).

Examples of such compounds include N,N-dimethylaminoethyl methacrylate, N,N-diethylaminoethyl methacrylate, N,N-dimethylaminopropyl methacrylate, N,N-diethylaminopropyl methacrylate, N,N-dimethylaminoethyl acrylate, N,N-diethylaminoethyl acrylate, N,N-dimethylaminopropyl acrylate, N,N-diethylaminopropyl acrylate, N,N-dimethylaminoethyl acrylamide and N,N-dimethylaminoethylmethacrylamide. These are used individually or in combination of two or more.

To introduce a carbon—carbon unsaturated double bond through an ionic bond, the amount of the acrylic compound having an amino group is preferably 1 to 200% by weight, more preferably 5 to 150% by weight of the starting polyamic acid, namely the compound of the general formula (7) wherein both $R^7$ and $R^8$ are OH. If it is less than 1% by weight, photosensitivity may be lowered, and if more than 200% by weight, heat-resistance and the mechanical properties of films may be deteriorated.

The production of polyimide precursors having ionic bonds by the above-described method may be achieved by mixing the above-described tetracarboxylic dianhydride and diamine to undergo ring-opening addition polymerization, and then mixing the resulting polyamic acid with the acrylic compound having an amino group.

Organic solvents to be used in the above-described production of polyimide precursors, such as the ring-opening addition polymerization, are preferably polar solvents which completely dissolve the product polyimide precursors, such as N-methyl-2-pyrrolidone, N,N-dimethylacetamide, N,N-dimethylformamide, dimethyl sulfoxide, tetramethylurea, hexamethylphophortriamide and γ-butyrolactone.

Besides the polar solvents, ketones, esters, lactones, ethers, halogenated hydrocarbons and hydrocarbons may be used, such as acetone, diethyl ketone, methyl ethyl ketone, methyl isobutyl ketone, cyclohexanone, methyl acetate, ethyl acetate, butyl acetate, diethyl oxalate, diethyl malonate, diethyl ether, ethylene glycol dimethyl ether, diethylene glycol dimethyl ether, tetrahydrofuran, dichloromethane, 1,2-dichloroethane, 1,4-dichlorobutane, trichloroethane, chlorobenzene, o-dichlorobenzene, hexane, heptane, octane, benzene, toluene and xylene.

These organic solvents are used individually or in combination of two or more.

The introduction of a carbon—carbon unsaturated double bond through an ester bond gives polyamidates. In this method, first a tetracarboxylate compound is synthesized. For example, the tetracarboxylate is synthesized by mixing the above-described tetracarboxylic dianhydride and an unsaturated alcohol compound in an organic solvent in the presence of a base.

Preferred unsaturated alcohol compounds are hydroxyalkyl acrylate or methacrylate having an alkylene chain of 1 to 10 carbon atoms, such as hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate and hydroxybutyl methacrylate.

In cases where Y in the general formula (7), preferably the general formula (9), is introduced by using a diamine having a phenolic hydroxyl group or a carboxylic group to prepare a polyimide precursor suited to positive, photosensitive resin compositions or the like, $R^7$ and $R^8$ each preferably are a monovalent hydrocarbon group (more preferably an alkyl group of 1 to 10 carbon atoms) linked through an oxygen atom. The polyimide precursor is another polyamidate, and obtainable by the same process as described above using an alcohol compound of a different kind.

Examples of such alcohol compound include alkyl alcohols of 1 to 10 carbon atoms, such as methanol, ethanol, n-propyl alcohol, isopropyl alcohol, n-butyl alcohol, sec-butyl alcohol, tert-butyl alcohol, isobutyl alcohol, 1-pentanol, 2-pentanol, 3-pentanol, isoamyl alcohol, 1-hexanol, 2-hexanol or 3-hexanol. These are used individually or in combination of two or more.

In the synthesis of tetracarboxylic acid diesters, the ratio of the tetracarboxylic dianhydride to the alcohol compound is preferably between 1/2 and 1/2.5, as the molar ratio of the former/the latter, most preferably 1/2. The ratio of the tetracarboxylic dianhydride to the base is preferably between 1/0.001 and 1/3, as the molar ratio of the former/the latter, more preferably between 1/0.005 and 1/2. The reaction temperature is preferably 10 to 60° C., and the reaction time is preferably 3 to 24 hours.

Subsequently a tetracarboxylic acid diester dihalide is synthesized by any known method, for example, by the reaction of a tetracarboxylic acid diester dissolved in an organic solvent with thionyl chloride added dropwise thereto. The ratio of the tetracarboxylic acid diester to thionyl chloride is preferably between 1/1.1 and 1/2.5, as the molar ratio of the former/the latter, more preferably between 1/1.5 and 1/2.2. The reaction temperature is preferably −20 to 40° C., and the reaction time is preferably 1 to 10 hours.

Polyamidates are obtainable by dissolving a diamine and a dehalogenating agent such as pyridine in an organic solvent, adding dropwise a tetracarboxylic acid diester dihalide dissolved in an organic solvent to conduct a reaction, pouring the reaction mixture into a bad solvent such as water, and filtering and drying the precipitate. The molar ratio of sum total of diamines to the tetracarboxylic acid diester dihalide is preferably between 0.6/1 and 1/0.6, as the molar ratio of the former/the latter, more preferably between 0.7/1 and 1/0.7. The reaction temperature is preferably −20 to 40° C., and the reaction time is preferably 1 to 10 hours. The ratio of the dehalogenating agent to the tetracarboxylic acid diester dihalide is preferably between 1.8/1 and 2.2/1, as the molar ratio of the former/the latter, more preferably between 1.9/1 and 2.1/1.

$R^7$ and $R^8$ in the polyimide precursor of the invention may also be a hydrocarbon group linked through a nitrogen atom. In such a case, the polyimide precursor is a polyamic acid amide. It is obtainable by the above-described process for preparing polyamidates, except the alcohol compound is replaced by a monoamine compound, such as methyl amine, ethyl amine, n-propyl amine, isopropyl amine, n-butyl amine, sec-butyl amine, tert-butyl amine, isobutyl amine, 1-pentyl amine, 2-pentyl amine, 3-pentyl amine, isoamyl amine, 1-hexyl amine, 2-hexyl amine, 3-hexyl amine, morpholine, aniline or benzyl amine.

The molecular weight of the polyimide precursors of the invention to be used for photosensitive resin compositions is not particularly limited, and is preferably 20,000 to 100,000 in weight average molecular weight, as measured using an E-type viscometer.

(C) Polyimides

The polyimide of the invention has the repetitive units of the general formula (11). It may be produced by any method, for example by imidation ring closure of the polyimide precursor of the invention.

Imidation ring closure is typically achieved with heat.

Heating conditions are not particularly limited, and preferred temperature is between 80 to 450° C. The ring closure at temperatures lower than 80° C. may be slow, and heating at temperatures higher than 450° C. may deteriorate the product polyimide.

The heating time is preferably 10 to 100 minutes. A heating time less than 10 minutes may result in an insufficient ring closure, and a heating time longer than 100 minutes may deteriorate the product polyimide or aggravate the working efficiency.

Many polyimides of the invention are insoluble in solvents, causing difficulty in direct measurement of molecular weight. If direct measurement is possible, polyimides of the invention preferably have a weight average molecular weight of 20,000 to 100,000, and if not, they preferably are produced from precursors, such as the above-described polyimide precursors, having the same weight average molecular weight.

(D) Resin Compositions

The resin composition of the invention is obtainable, for example, by dissolving the polyimide precursor or polyimide of the invention in an organic solvent as described above and adding other optional components, if any. The resin composition is particularly suitable for forming surface-protecting films or interlayer insulating films in electronic parts.

Preferred polyimide precursors and polyimides are polyimide precursors of the general formula (8) and the polyimide of the general formula (12).

The amount of organic solvents is not particularly limited, and is preferably 50 to 85% by weight of the total resin composition.

The above-described optional components are not particularly limited, and examples are adhesiveness promoters, such as organic silane compounds, aluminum chelate compounds and polyamic acids having polysiloxane linkages. The amount of such components is not particularly limited, and, for example, may be at most 10% by weight of the total resin composition.

The resin composition may be applied onto a base, such as a silicon wafer, a metal substrate or a ceramic substrate, by dipping, spraying, screen printing, spin coating or the like, and heated thereon to remove most of solvents, to form non-tacky coating film. The thickness of the coating film is not particularly limited. To produce electronic parts having good circuit properties, it is preferably 4 to 50 μm, more preferably 6 to 40 μm, particularly preferably 10 to 40 μm, extremely preferably 20 to 35 μm.

Because of the rigid molecule structure of the polyimide or polyimide precursor, the polyimide film-or polyimide precursor film formed from the resin composition of the invention exhibits low thermal expansion. Having excellent transparency to light such as i-line, it is also excellent in the properties requisite of photosensitive materials.

When the film is a polyimide precursor, a high-heat-resistant polyimide film is obtainable by heating it.

The heating temperature is preferably 150 to 500° C., more preferably 200 to 400° C. Heating at a temperature lower than 150° C. or higher than 500° C. may deteriorate the mechanical and thermal properties of the polyimide film.

Heating time is preferably 0.05 to 10 hours. If the heating time is less than 0.05 hour or longer than 10 hours, the mechanical and thermal properties of the polyimide film may be deteriorated.

Being excellent in heat-resistance, the film is useful for protecting films or insulating films in various electronic parts requiring excellent heat-resistance, such as surface-protecting films or interlayer insulating films in semiconductor devices, or interlayer insulating films in multilayer wiring boards.

(E) Electronic Parts (a)

The electronic part (a) of the invention has a film of the polyimide having repetitive units of the general formula (11), preferably the general formula (12). Examples of the electronic part (a) of the invention include semiconductor devices, for example semiconductor substrates such as silicon chips having circuits fabricated thereon, and multilayer wiring boards, which have the above-described polyimide film as surface-protecting films or interlayer insulating film.

One example of the process for fabricating the electronic part (a) of the invention is mentioned below.

FIG. 4A to FIG. 4E show a process for fabricating a semiconductor device having a multi-layered interconnection structure. As illustrated, the semiconductor substrate 1 of, for example, Si, which has a circuit element thereon, is coated with the protective film 2 of, for example, silicon oxide, except for the predetermined part of the circuit element, and the first conductor layer 3 is formed on the exposed circuit element. The semiconductor substrate 1 is coated with the interlayer insulating film 4 of the polyimide of the invention by forming a patterned layer of the resin composition of the invention, followed by heating (step of FIG. 4A).

Figure 4A:
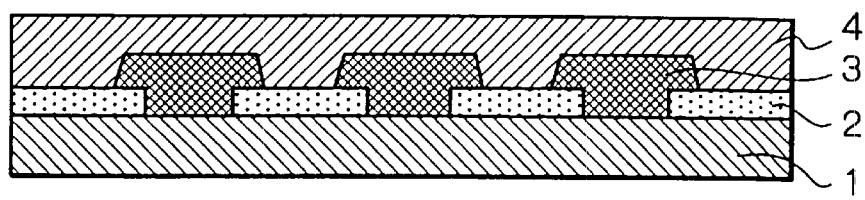
FIG. 4A to FIG. 4E show a process for fabricating a semiconductor device having a multilayered interconnection structure.
Figure 4B:
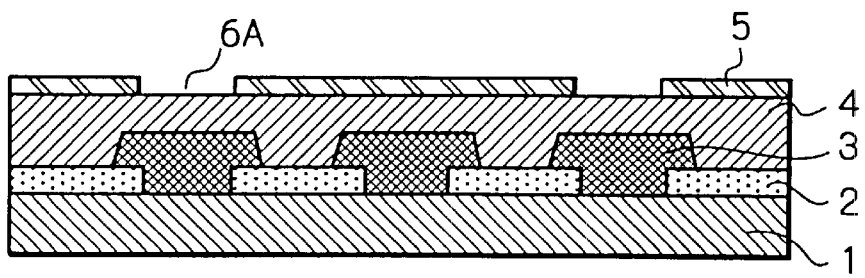
Figure 4C:
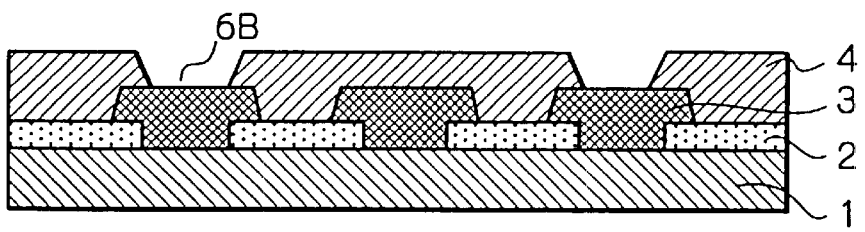

Next, the rubber chloride-based or phenol-novolak-based, photosensitive resin layer 5 is formed on the interlayer insulating film 4 by a spin-coating method, and the windows 6A are formed, through which a predetermined part of the interlayer insulating film 4 is exposed outside, by a known photo-engraving technique (step of FIG. 4B).

The interlayer insulating film 4 below each window 6A is selectively etched by a dry etching method using a gas such as oxygen or carbon tetrafluoride, to give the windows 6B. Next, the photosensitive resin layer 5 is completely removed with an etching solution capable of etching the photosensitive resin layer 5 only, but not etching the first conductor layer 3 exposed outside through the windows 6B (step of FIG. 4C).

Figure 4D:
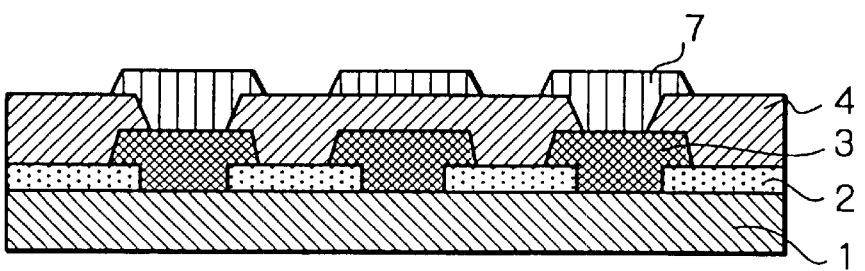

Next, by a known photoengraving technique, the second conductor layer 7 is formed, which is completely electrically connected with the first conductor layer 3 (step of FIG. 4D).

For forming a multi-layered interconnection structure having three or more layers, the steps illustrated are repeated for each layer.

Figure 4E:
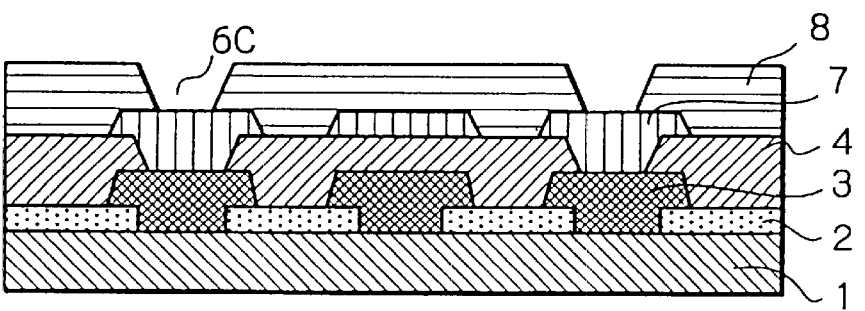

Next, the surface-protecting film 8 is formed (step of FIG. 4E). The surface-protecting film 8 is formed by the same method using the resin composition of the invention as that employed for the production of the interlayer insulating film 4. The polyimide film protects the conductor layer from external stress, α-rays and others, and the semiconductor device thus fabricated has good reliability.

(F) Photosensitive Resin Compositions

The photosensitive resin composition of the invention contains a polyimide precursor having the repetitive units of the general formula (7), preferably the general formula (9).

The photosensitive resin composition preferably contains a polyimide precursor having repetitive units of the general formula (9) wherein the divalent organic group for Y has the structure of the general formula (10):

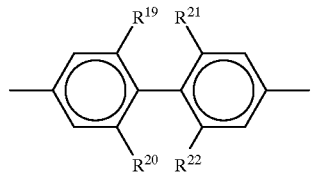

(10)

wherein $R^9$, $R^{20}$, $R^{21}$ and $R^{22}$ are as defined above.

More preferably, the photosensitive resin composition of the invention contains the above-described polyimide precursors suited to photosensitive resin compositions. Proper polyimide precursors must be used depending on the intended types, positive type or negative type.

For example, as mentioned above, negative, photosensitive resin compositions preferably contain polyimide precursors which have repetitive units of the general formula (7), preferably the general formula (9), wherein at least one of $R^7$ and $R^8$ is a monovalent organic group having a carbon—carbon unsaturated double bond.

Positive, photosensitive resin compositions preferably contain polyimide precursors having repetitive units of the general formula (7), preferably the general formula (9), wherein Y is a divalent organic group having a carboxyl group or a phenolic hydroxyl group, or wherein $R^7$ and $R^8$ are hydroxyl groups, as combined with a compound capable of generating an acid when exposed to light.

Negative, photosensitive resin compositions, if desired, may optionally contain a photopolymerization initiator, as combined with the polyimide precursor.

Examples of the photopolymerization initiator include Michler's ketone, benzoin methyl ether, benzoin ethyl ether, benzoin isopropyl ether, 2-t-butylanthraquinone, 2-ethylanthraquinone, 4,4-bis(diethylamino)benzophenone, acetophenone, benzophenone, thioxanthone, 2,2-dimethoxy-2-phenylacetophnone, 1-hydroxycyclohexyl phenyl ketone, 2-methyl-[$^4$-(methylthio)phenyl]-2-morpholino-1-propanone, benzyl, diphenyl disulfide, phenanthrenequinone, 2-isopropylthioxanthone, rivoflavin tetrabutyrate, 2,6-bis(p-diethylaminobenzal)-4-methyl-4-azacyclohexanone, N-ethyl-N-(p-chlorophenyl)glycine, N-phenyldiethanolamine, 2-(o-ethoxycarbonyl)oxyimino-1, 3-diphenylpropanedione, 1-phenyl-2-(o-ethoxycarbonyl) oxyiminopropane-1-one, 1,3-diphenyl-1,2,3-propanetrione-2-(o-ethoxycarbonyl)oxime, 3,3,4,4-tetra(t-butylperoxycarbonyl)benzophenone, 3,3-carbonylbis(7-diethylaminocoumarin) and bis(cyclopentadienyl)-bis[2,6-difluoro-3-(pyr-1-yl)phenyl]titanium. These are used individually or in combination of two or more.

The amount of the photopolymerization initiator is preferably 0.01 to 30% by weight, more preferably 0.05 to 10% by weight based on the polyimide precursor having the repetitive units of the general formula (7), preferably the general formula (9). If it is less than 0.01% by weight, photosensitivity may be lowered, and if more than 30% by weight, the mechanical properties of films may be deteriorated.

Negative, photosensitive resin compositions, if desired, may optionally contain an addition-polymerizable compound having a carbon—carbon unsaturated double bond.

Examples of the addition-polymerizable compound include diethylene glycol diacrylate, triethylene glycol diacrylate, tetraethylene glycol diacrylate, diethylene glycol dimethacrylate, triethylene glycol dimethacrylate, tetraethylene glycol dimethacrylate, trimethylolpropane diacrylate, trimethylolpropane triacrylate, trimethylolpropane dimethacrylate, trimethylolpropane trimethacrylate, 1,4-butanediol diacrylate, 1,6-hexanediol diacrylate, 1,4-butanediol dimethacrylate, 1,6-hexanediol methacrylate, pentaerythritol triacrylate, pentaerythritol tetraacrylate, pentaerythritol trimethacrylate, pentaerythritol tetramethacrylate, styrene, divinylbenzene, 4-vinyltoluene, 4-vinylpyridine, N-vinylpyrrolidone, 2-hydroxyethyl acrylate, 2-hydroxyethyl methacrylate, 1,3-acryloyloxy-2-hydroxypropane, 1,3-methacryloyloxy-2-hydroxypropane, methylenebisacrylamide, N,N-dimethylacrylamide, N-methylolacrylamide and dimethylaminopropyl methacrylate. These may be used individually or in combination of two or more.

The amount of the addition-polymerizable compound is preferably 1 to 200% by weight, based on the amount of the polyimide precursor having repetitive units of the general formula (7), preferably the general formula (9). If it is less than 1% by weight, photosensitive properties including solubility in developer may be deteriorated, and if more than 200% by weight, the mechanical properties of films may be deteriorated.

If desired, negative, photosensitive resin compositions may also contain an azide compound. Examples of such a compound are mentioned below.

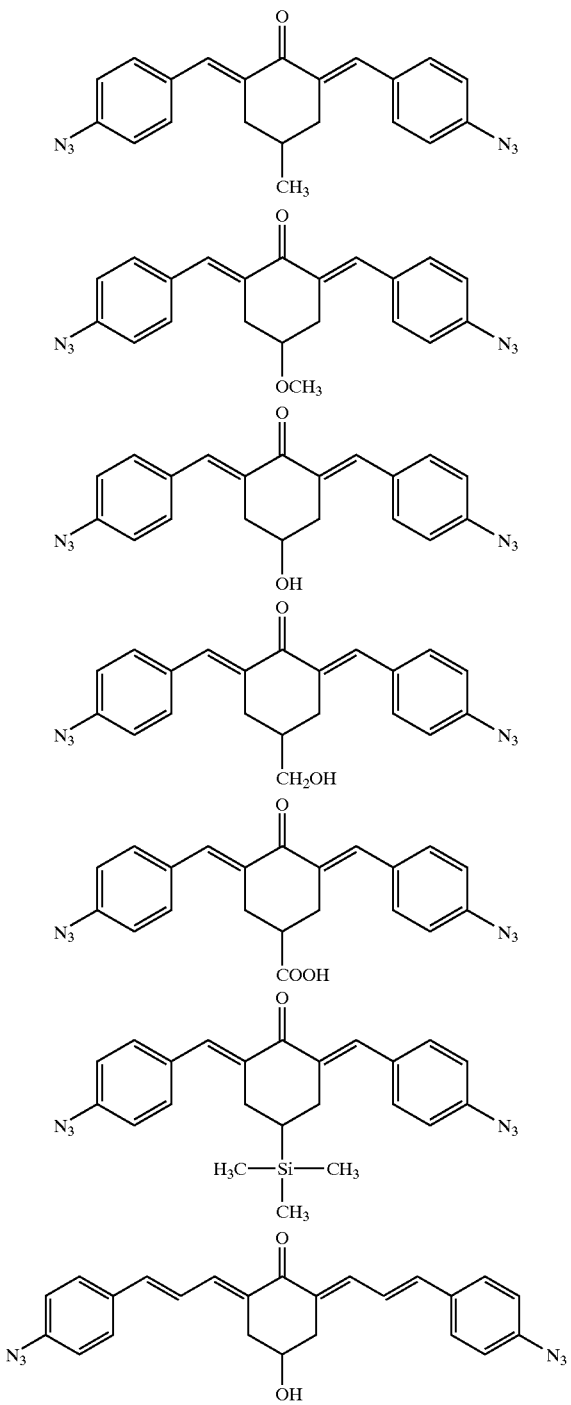

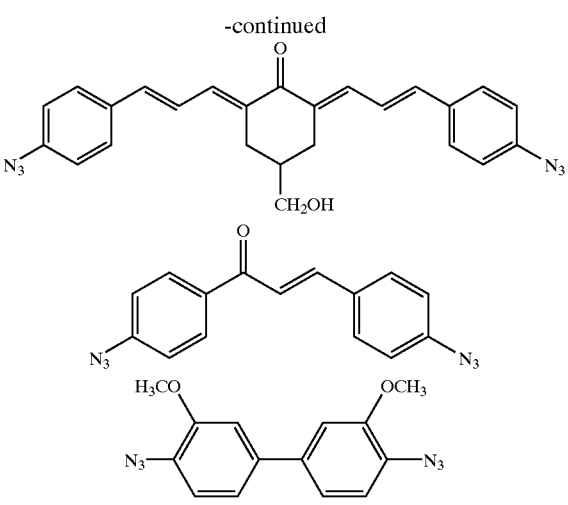

These may be used individually or in combination of two or more.

The amount of the azide compound is preferably 0.01 to 30% by weight, more preferably 0.05 to 10% by weight, based on the amount of the polyimide precursor having the repetitive units of the general formula (7), preferably the general formula (9). If it is less than 0.01% by weight, photosensitivity may be deteriorated, and if more than 30% by weight, the mechanical properties of films may be deteriorated.

To improve the storage stability, negative, photosensitive resin compositions may contain a radical polymerization inhibitor or a radical polymerization retarder.

Examples of the radical polymerization inhibitor and radical polymerization retarder include p-methoxyphenol, diphenyl-p-benzoquinone, benzoquinone, hydroquinone, pyrogallol, phenothiazine, resorcinol, o-dinitrobenzene, p-dinitrobenzene, m-dinitrobenzene, phenanthraquinone, N-phenyl-1-naphthylamine, N-phenyl-2-naphthylamine, cuferron, phenothiazine, 2,5-toluquinone, tannic acid, p-benzylaminophenol and nitrosamine. These are used individually or in combination of two or more.

The amount of the radical polymerization inhibitor or radical polymerization retarder is preferably 0.01 to 30% by weight, more preferably 0.05 to 10% by weight, based on the amount of the polyimide precursor having the repetitive units of the general formula (7), preferably the general formula (9). If it is less than 0.01% by weight, storage stability may become poor, and if more than 30% by weight, photosensitivity and the mechanical properties of films may be deteriorated.

To produce positive, photosensitive resin compositions, in general, a compound capable of generating an acid when exposed to light is used together with the polyimide precursor. The compound capable of generating an acid when exposed to light is a photosensitive agent. When exposed to light, this generates an acid, thereby increasing the solubility of the exposed area of the photosensitive resin composition in an aqueous alkaline solution. Examples of the compound include o-quinonediazide compounds, aryldiazonium salts, diaryliodonium salts and triarylsulfonium salts. Non-limitative but preferred examples are o-quinonediazide compounds as having high sensitivity.

O-quinonediazide compounds are produced, for example, through condensation of an o-quinonediazidosulfonyl chloride with a hydroxy compound and/or an amino compound in the presence of a dehydrochlorinating agent.

Examples of the o-quinonediazidosulfonyl chloride include 1,2-benzoquinone-2-diazido-4-sulfonyl chloride, 1,2-naphthoquinone-2-diazido-5-sulfonyl chloride and 1,2-naphthoquinone-2-diazido-4-sulfonyl chloride.

Examples of the hydroxy compounds include hydroquinone, resorcinol, pyrogallol, bisphenol A, bis(4-hydroxyphenyl)methane, 2,2-bis(4-hydroxyphenyl) hexafluoropropane, 2,3,4-trihydroxybenzophenone, 2,3,4,4'-tetrahydroxybenzophenone, 2,2',4,4'-tetrahydroxybenzophenone, 2,3,4,2',3'-pentahydroxybenzophenone, 2,3,4,3',4',5'-hexahydroxybenzophenone, bis(2,3,4-trihydroxyphenyl) methane, 2,2-bis(2,3,4-trihydroxyphenyl)propane, 4b,5,9b, 10-tetrahydro-1,3,6,8-tetrahydroxy-5,10-dimethylindeno[2, 1-a]indene, tris(4-hydroxyphenyl)methane and 1,1,1- or 1,1, 2-tris(4-hydroxyphenyl)ethane.

Examples of the amino compound include p-phenylenediamine, m-phenylenediamine, 4,4'-diaminodiphenyl ether, 4,4'-diaminodiphenylmethane, 4,4'-diaminodiphenyl sulfone, 4,4'-diaminodiphenyl sulfide, o-aminophenol, m-aminophenol, p-aminophenol, 3,3'-diamino-4,4'-dihydroxybiphenyl, 4,4'-diamino-3,3'-dihydroxybiphenyl, 2,2-bis(3-amino-4-hydroxyphenyl) propane, 2,2-bis(4-amino-3-hydroxyphenyl)propane, bis(3-amino-4-hydroxyphenyl) sulfone, bis(4-amino-3-hydroxyphenyl) sulfone, 2,2-bis(3-amino-4-hydroxyphenyl) hexafluoropropane and 2,2-bis(4-amino-3-hydroxyphenyl) hexafluoropropane.

For their condensation, it is desirable that the o-quinonediazidosulfonyl chloride and the hydroxy compound and/or the amino compound are so controlled that the sum total of the hydroxy group and the amino group is from 0.5 to 1 equivalent relative to one mol of the o-quinonediazidosulfonyl chloride. Preferably, the ratio of the dehydrochlorinating agent to the o-quinonediazidosulfonyl chloride is between 0.95/1 and 1/0.95. The reaction temperature is preferably 0 to 40° C., and the reaction time is preferably 1 to 10 hours.

Examples of reaction solvents usable in the condensation include dioxane, acetone, methyl ethyl ketone, tetrahydrofuran, diethyl ether and N-methylpyrrolidone. Examples of the dehydrochlorinating agent include sodium carbonate, sodium hydroxide, sodium hydrogencarbonate, potassium carbonate, potassium hydroxide, trimethylamine, triethylamine and pyridine.

The amount of the compound capable of generating an acid when exposed to light is preferably 5 to 100 parts by weight, more preferably 10 to 40 parts by weight, relative to 100 parts by weight of the polyimide precursor having the repetitive units of the general formula (7), preferably the general formula (9), in view of the thickness of the developed films, and of the sensitivity of the positive, photosensitive resin composition.

The photosensitive resin composition of the invention may be prepared as a solution by dissolving the polyimide precursor having the repetitive units of the general formula (7), preferably the general formula (9), in a solvent, followed by further dissolving any other optional components therein.

Examples of the solvent are aprotic polar solvents such as N-methyl-2-pyrrolidone, N,N-dimethylformamide, N,N-dimethylacetamide, dimethyl sulfoxide, hexamethylphosphoramide, tetramethylene sulfone, γ-butyrolactone, cyclohexanone or cyclopentanone, which are used individually or in combination of two or more.

To improve the adhesiveness of cured film to substrates, the photosensitive composition of the invention may further contain any one of organic silane compounds, aluminum chelate compounds and silicon-containing polyamic acids.

Examples of the organic silane compounds include γ-aminopropyltrimethoxysilane, γ-aminopropyltriethoxysilane, vinyltriethoxysilane, γ-glycidoxypropyltriethoxysilane, γ-methacryloxypropyltrimethoxysilane and 3-isocyanatopropyltriethoxysilane. Examples of the aluminum chelate compounds include tris(acetylacetonato) aluminum and acetylacetatoaluminum diisopropylate.

(G) Production of Relief Patterns
Step of Applying a Photosensitive Resin Composition onto a Substrate and Drying it thereon The photosensitive resin composition of the invention may be formed into a non-tacky coating film by applying it onto a substrate, such as a silicon wafer, a metal substrate or a ceramic substrate, by dipping, spraying, screen printing or spin coating, and then drying thereon by removing most of the solvent with heat. Non-limitative but preferred thickness of the coating is 4 to 50 $\mu$m, more preferably 6 to 40 $\mu$m, particularly preferably 10 to 40 $\mu$m, especially preferably 20 to 35 $\mu$m, in view of the properties of circuits.

Exposing Step and Developing Step

Desired relief patterns are obtainable, for example, by the patterned exposure of the coating film to active rays or actinic rays via an equally patterned mask, followed by development of the unexposed or exposed area with a developer to dissolve and remove the area.

Although exposure to i-line using i-line steppers is suited to the photosensitive resin composition of the invention, other exposure techniques may also be used, for example, exposure to other active or actinic rays, for example, those from other aligners using ultra-high-pressure mercury-vapor lamps, such as contact/proximity aligners, mirror-projection aligners or g-line steppers, other ultraviolet rays, visible rays, X-rays or electron rays. The exposure is preferably 100 to 1,000 mJ/cm$^2$.

Examples of usable developer include organic solvent developers, for example good solvents, such as N,N-dimethylformamide, N,N-dimethylacetamide or N-methyl-2-pyrrolidone, and mixtures of good solvents with bad solvents, such as lower alcohols, ketones, water, alicyclic hydrocarbons including cyclopentane or aromatic hydrocarbons; and alkaline developers. When polyimide precursors soluble to alkalis are used, aqueous alkaline solutions may be used. Examples of usable aqueous alkaline solutions include aqueous solutions of sodium hydroxide, potassium hydroxide, sodium silicate or tetramethylammonium hydroxide with a concentration of 5 wt % or less, preferably 1.5 to 3.0 wt %, with 1.5 to 3.0 wt % aqueous tetramethylammonium hydroxide solution particularly preferred.

Additives such as surfactants may optionally be added to the above-described developers. The amount of each additive is preferably 0.01 to 10 parts by weight, more preferably 0.1 to 5 parts by weight, relative to 100 parts by weight of the developer.

After development, the patterns are preferably stabilized by rinsing it with water or a bad solvent and then drying at around 100° C.

Heating Step

A patterned, high-heat-resistant polyimide film is formed by heating the relief pattern.

The heating temperature is preferably 150 to 500° C., more preferably 200 to 400° C. If it is lower than 150° C. or higher than 500° C., the polyimide film may have poor mechanical and thermal properties.

The heating time is preferably 0.05 to 10 hours. If it is less than 0.05 hours or more than 10 hours, the polyimide film may have poor mechanical and thermal properties.

The photosensitive resin composition of the invention may be used in electronic parts such as semiconductor devices or multilayer wiring boards, by forming it into relief patterns as described above. Concretely, it may be used for forming surface-protecting films and interlayer insulating films in semiconductor devices, or for forming interlayer insulating films in multilayer wiring boards.

FIG. 4A to FIG. 4E show a process for fabricating a semiconductor device having a multi-layered interconnection structure. As illustrated, the semiconductor substrate 1 of, for example, Si, which has a circuit element thereon, is coated with the protective film 2 of, for example, silicon oxide, except for the predetermined part of the circuit element, and the first conductor layer 3 is formed on the exposed circuit element. The semiconductor substrate is coated with the interlayer insulating film 4 of, for example, a polyimide resin, by a spin-coating method or the like (step of FIG. 4A).

Next, the rubber chloride-based or phenol-novolak-based, photosensitive resin layer 5 is formed on the interlayer insulating film 4 by a spin-coating method, and the windows 6A are formed, through which a predetermined part of the interlayer insulating film 4 is exposed outside, by a known photo-engraving technique (step of FIG. 4B).

The interlayer insulating film 4 below each window 6A is selectively etched by a dry etching method using a gas such as oxygen or carbon tetrafluoride, to open the windows 6B. Next, the photosensitive resin layer 5 is completely removed with an etching solution capable of etching the photosensitive resin layer 5 only, but not etching the first conductor layer 3 exposed outside through the windows 6B (step of FIG. 4C).

Next, by a known photoengraving technique, the second conductor layer 7 is formed, which is completely electrically connected with the first conductor layer 3 (step of FIG. 4D).

For forming a multi-layered interconnection structure having three or more layers, the steps illustrated are repeated for each layer.

Next, the surface-protecting film 8 is formed (step of FIG. 4E). In this example illustrated, the surface-protecting film 8 is formed by a applying the photosensitive polymer composition of the invention onto the wafer by spin-coating, drying it thereon, exposing it to light via a mask having a pattern for the windows 6C to be formed in predetermined parts, developing it with an aqueous alkaline solution to give a predetermined pattern, and then heating the pattern to form a polyimide film. The polyimide film protects the conductor layer from external stress, a-rays and others, and the semiconductor device thus fabricated has good reliability.

In the example illustrated, the interlayer insulating film 4 may also be formed directly from the photosensitive polymer composition of the invention without forming the photosensitive resin layer 5.

(H) Electronic Parts (b)

The electronic parts (b) of the invention are not specifically limited and may be of various structures, so far as they have surface-protecting films or interlayer insulating films which are formed from the photosensitive resin composition of the invention by the above-described method of forming relief patterns. Examples are semiconductor devices comprising a semiconductor substrate such as a silicon chip having circuits fabricated thereon, and multilayer wiring boards, which have relief patterns made from the photosensitive resin composition of the invention as surface-protecting films or interlayer insulating films.

EXAMPLES 1 TO 8 AND COMPARATIVE EXAMPLES 1 TO 5

Example 1

In this example, a tetracarboxylic dianhydride was synthesized according to the following reaction scheme.

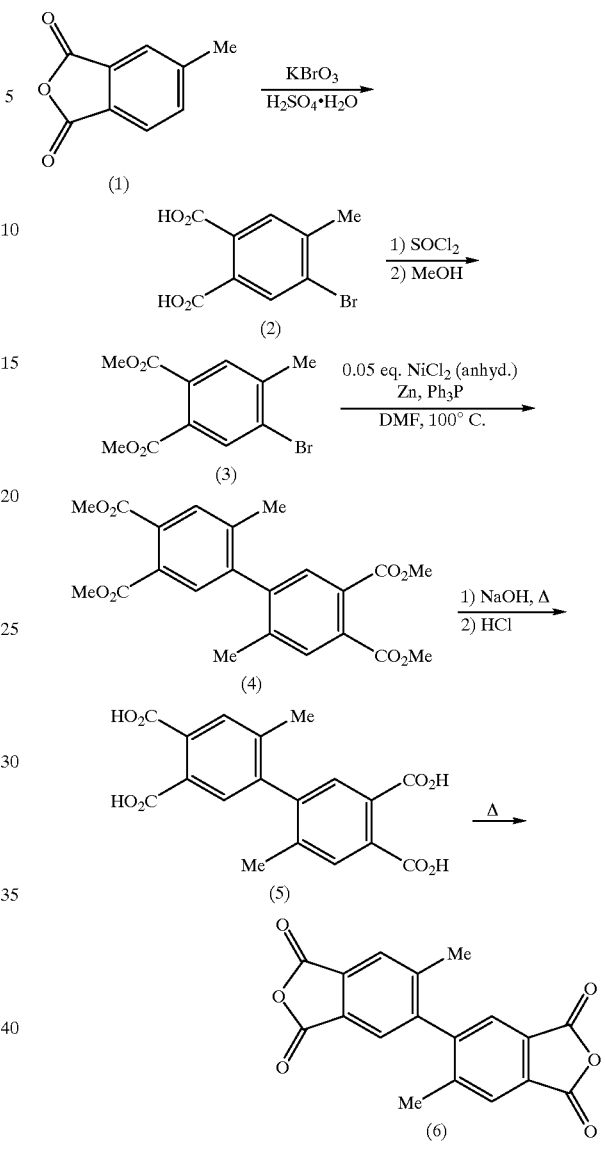

A suspension of 4-methylphthalic anhydride (1) (58.8 g, 0.363 mol) and potassium bromate (66.7 g, 0.400 mol) in 250 ml of water was heated to 90° C., and after the removal of the heating bath used, 250 ml of concentrated sulfuric acid was slowly added dropwise with vigorous stirring. After the completion of the dropping, the heating bath was attached again to heat the mixture at 90 to 100° C. for 3 hours with stirring. The mixture was then allowed to cool down to ambient temperature, and the precipitated solid was separated on a filter, and rinsed with cold water. The filtrate was extracted with three portions of ether. The combined organic phase was washed with successive water and saturated saline solution, and dried over anhydrous sodium sulfate. The ether solution was then concentrated to obtain a solid. The solid was combined with the solid separated previously on the filter were combined, and water was separated therefrom as a toluene azeotrope, to obtain a crude 5-bromo-4-methylphthalic acid (2).

100 ml of thionyl chloride was added to the crude 5-bromo-4-methylphthalic acid (2), and heated to reflux for 4 hours. After cooling down to ambient temperature, 200 ml of methanol was added thereto and heated to reflux for 5 hours. After cooling down to ambient temperature, methanol was distilled away under reduced pressure. The oily residue was distilled to obtain methyl 5-bromo-4-methylphthalate (3) (bp. 156–159° C./5 mmHg, 54.3 g, 52% yield based on 4-methylphthalic anhydride).

A suspension of anhydrous nickel chloride (0.84 g, 6.5 rnmmol), bipyridyl (1.02 g, 6.5 mmol), triphenylphosphine (11.0 g, 41.9 mmol) and zinc dust (13.1 g, 0.200 g atom) in 80 ml of dimethylformamide (DMF) was heated under nitrogen at 60° C. until deep brown coloration was observed. It was then heated up to 100° C., and a solution of methyl 5-bromo-4-methylphthalate (3) (33.2 g, 0.116 mol) in 20 ml of DMF was added dropwise. The mixture was stirred at 100° C. for 8 hours, cooled down to ambient temperature, and poured into ice water. The mixture was filtered through sellite, extracted with ether, washed with water, and dried over anhydrous sodium sulfate. The ether solution was dried into an oily concentrate and then purified by silica gel column chromatography, to obtain a tetraester (4) (12.65 g, 30.6 mmol, 53% yield). Crystallization from methanol afforded a higher purity.

In larger scale reactions, the purification by column chromatography may be omitted by replacing it with solidification of the crude product and washing the solid with ether or a mixture of ether with a small quantity of hexane.

The tetraester (4) (6.54 g, 15.8 mmol) and 90 ml of 4 mol/l aqueous sodium hydroxide solution were heated to reflux for 8 hours. When the mixture was allowed to cool down to ambient temperature and 40 ml of concentrated hydrochloric acid was slowly added while cooling with ice, white solid was precipitated. The precipitate was filtered and dried under vacuum, to obtain a tetracarboxylic acid (5) (6,6'-dimethyl-3,3',4,4'-biphenyltetracarboxylic acid). The solid was kept at 180° C. for 6 hours under reduced pressure (5 mmHg) to obtain an acid anhydride (6) (4.78 g, 14.8 mmol, 94 wt % yield based on the tetraester (4)).

Figure 2:
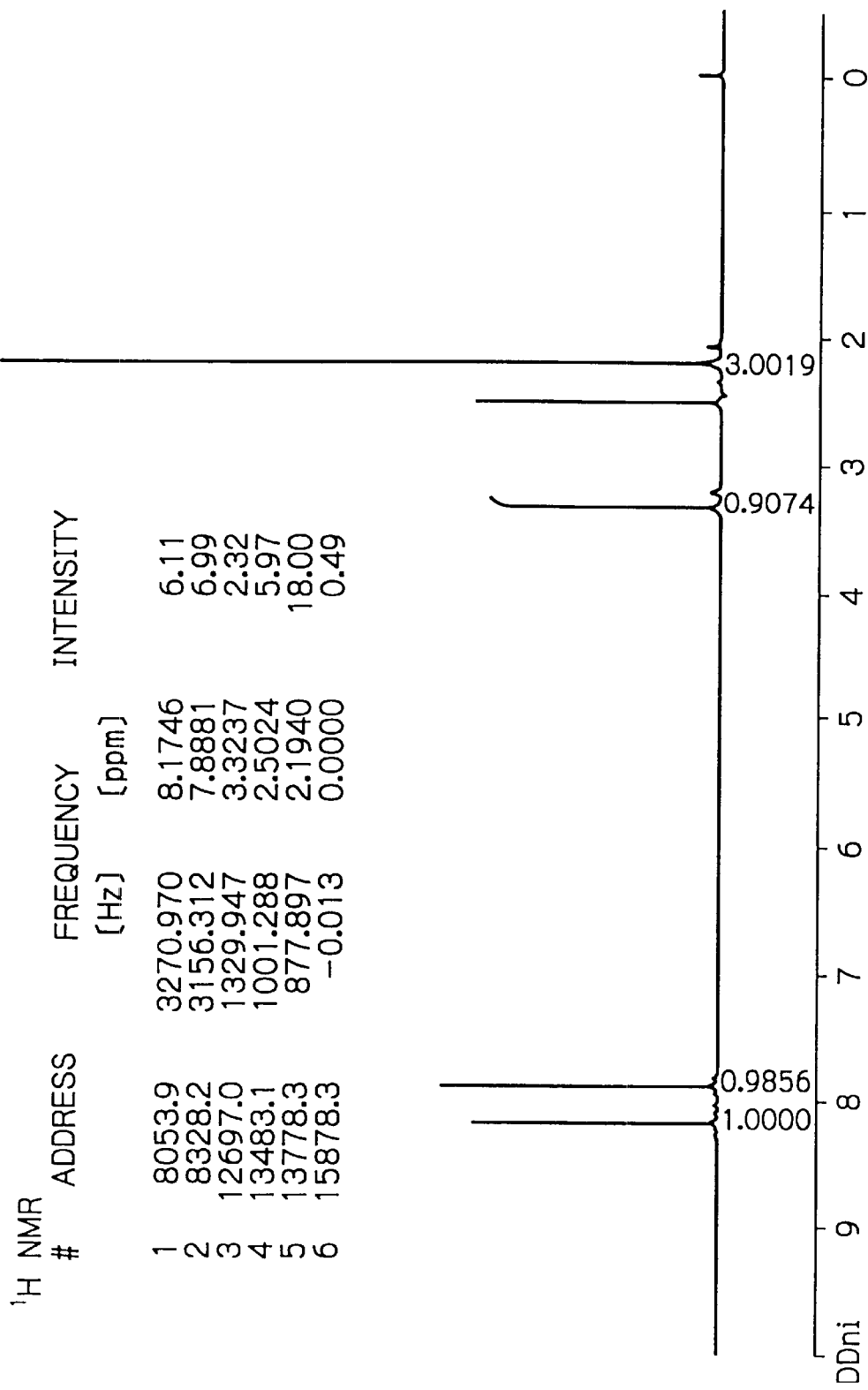
FIG. 2 is a diagram showing an $^1$H-NMR spectrum of a typical tetracarboxylic dianhydride according to the invention.
Figure 3:
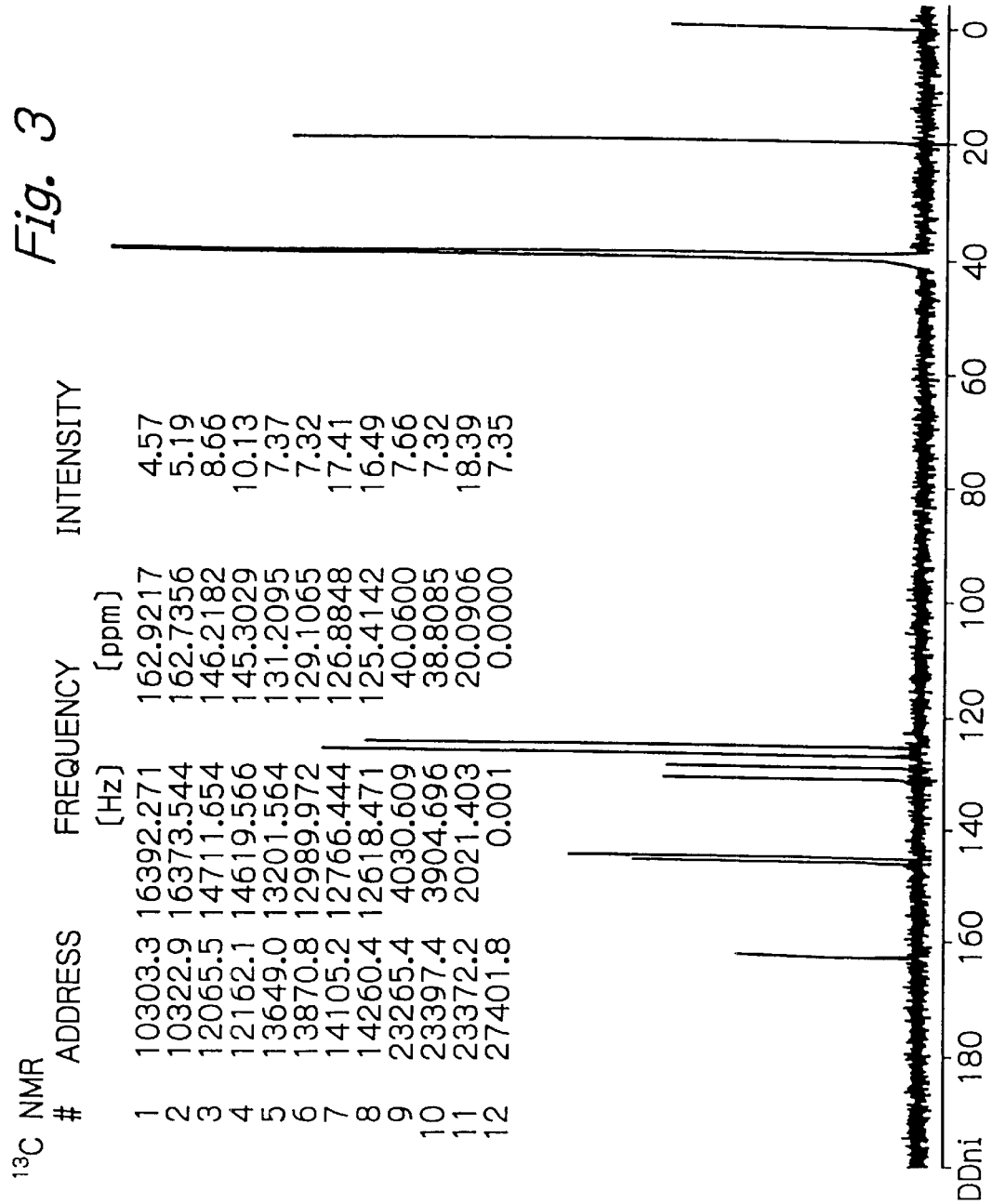
FIG. 3 is a diagram showing an $^{13}$C-NMR spectrum of a typical tetracarboxylic dianhydride according to the invention.

FIG. 1 shows an IR spectrum of the acid anhydride (6), FIG. 2 an $^1$H-NMR spectrum, FIG. 3 a $^{13}$C-NMR spectrum. The analytical data are as follows.

mp.: 235–236° C.

IR (KBr): 1849, 1784, 1323, 1257, 887, 737 cm$^{-1}$ $^1$H-NMR (DMSO-d$_6$): d=2.19 (6H,s), 7.89 (2H,s), 8.17 (2H,s)

$^{13}$C-NMR (DMSO-d$_6$): d=20.09, 125.41, 126.88, 129.11, 131.21, 145.30, 146.22, 162.74, 162.91

MS m/z 322

The tetracarboxylic acid and its dianhydride and derivatives of the invention is very useful as monomers for the production of polyimide precursors (polyamic acids), which have not only rigid structures ensuring low thermal expansion and excellent heat-resistance but also good i-line transmissivity enough for practical use.

Example 2

Synthesis of a Polyimide and its Precursor

Into a 100 ml-separable flask equipped with a stirrer were added 2.98 g of 4,4'-diamino-2,2'-dimethylbiphenyl and 22.5 g of N-methyl-2-pyrrolidone (NMP), and dissolved with stirring at ambient temperature. To the solution was added 4.52 g of 6,6'-dimethyl-3,3',4,4'-biphenyltetracarboxylic dianhydride, and stirred for 30 hours to give a viscous solution of a polyimide precursor.

The polyimide precursor had a weight average molecular weight of 70,000, as measured with an E-type viscometer.

The solution of the polyimide precursor was dried and subjected to measurement of an infrared absorption spectrum by a KBr method (Model JIR-100 produced by Japan Electron Co., Ltd.). The spectrum indicated an absorption due to C=O of amido groups in the vicinity of 1600 cm$^{-1}$ and an absorption due to N—H in the vicinity of 3300 cm$^{-1}$, indicating the following structure for the repetitive units of the polyimide precursor.

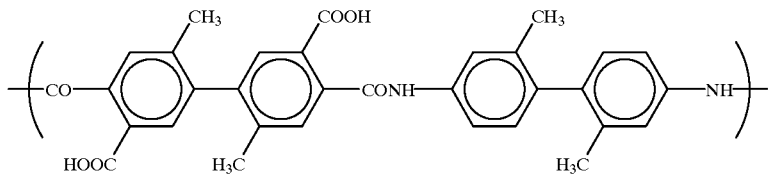

Subsequently, the solution was heated at 70° C. for 5 hours to give a polyimide precursor solution with a viscosity adjusted to 100 poise (solid content: 25 wt %), which was filtered, and dropped and applied onto a silicon wafer by spin-coating. The applied solution was heated on a hot plate at 90° C. for 150 seconds to form a coating film, and then cured with heat in a homogenizing furnace at 400° C. for 60 minutes to form a polyimide film having repetitive units of the following structure.

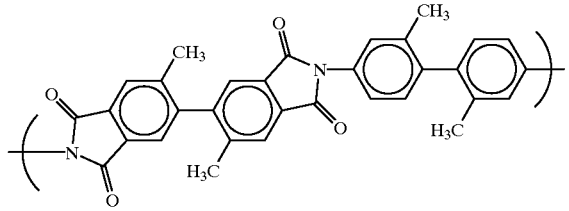

Example 3

Synthesis of a Polyimide and its Precursor

To a 100 ml-separable flask equipped with a stirrer were added 6.05 g of 9,9-bis(4-aminophenyl)fluorene and 22.5 g of N-methyl-2-pyrrolidone (NMP), and dissolved with stirring at ambient temperature. To the solution was added 5.61 g of 6,6'-dimethyl-3,3',4,4'-biphenyltetracarboxylic dianhydride, and stirred for 30 hours to obtain a viscous solution of a polyimide precursor.

The polyimide precursor had a weight average molecular weight of 50,000, as measured with an E-type viscometer.

The solution of the polyimide precursor was dried and subjected to measurement of an infrared absorption spectrum by a KBr method (Model JIR-100 produced by Japan Electron Co., Ltd.). The spectrum indicated an absorption due to C=O of amido groups in the vicinity of 1600 cm⁻¹ and an absorption due to N—H in the vicinity of 3300 cm⁻¹, indicating the following structure for the repetitive units of the polyimide precursor.

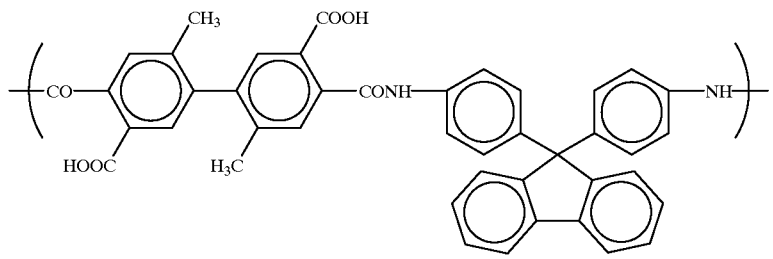

Subsequently, the solution was heated at 70° C. for 5 hours to give a polyimide precursor solution with a viscosity adjusted to 100 poise (solid content: 25 wt %), which was filtered, and dropped and applied onto a silicon wafer by spin-coating. The applied solution was heated on a hot plate to 90° C. for 150 seconds to form a coating film, and then cured with heat in a homogenizing furnace at 400° C. for 60 minutes to form a polyimide film having repetitive units of the following structure.

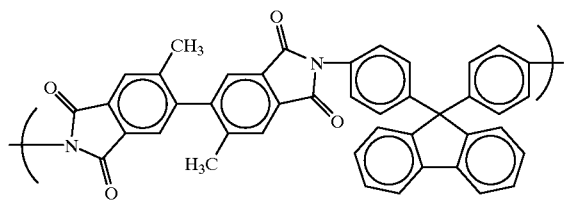

Comparative Example 1

A polyimide film was formed in the same manner as that in the above-described examples, except that 2.98 g of 4,4'-diamino-2,2'-dimethylbiphenyl and 4.34 g of 4,4'-oxydiphthalic dianhydride were used as the raw materials for a polyimide precursor.

Comparative Example 2

A polyimide film was formed in the same manner as that in the above-described examples, except that 2.98 g of 4,4'-diamino-2,2'-dimethylbiphenyl and 4.12 g of 3,3',4,4'-biphenyltetracarboxylic dianhydride were used as the raw materials for a polyimide precursor.

The i-line percent transmittances of coating films of the polyimide precursors prepared in Examples 1 and 2 and Comparative Examples 1 and 2 were measured, and the glass transition temperatures (Tg) of the polyimide films cured with heat were measured with a thermomechanical analyzer (TMA). The results are indicated in Table 1.

The measurement of i-line percent transmittance was conducted using a spectrophotometer on a 10 μm coating film formed by spin-coating each of the solutions of the polyimide precursors obtained as above, drying at 85° C. for 3 minutes, and at 105° C. for 3 minutes.

TABLE 1

|  | i-line percent transmittance | Tg (° C.) |
| --- | --- | --- |
| Example 1 | 54 | 430 |
| Example 2 | 62 | 390 |
| Comparative Example 1 | 56 | 290 |
| Comparative Example 2 | 7.6 | 360 |

The data given in Table 1 indicate that the polyimide precursors of Examples 1 and 2 have not only high 1-line percent transmittances but also have excellent heat-resistance after cured into polyimides.

Negative, Photosensitive Resin Compositions

Synthetic Examples 1, 2, 4 and 5

In each examples, to a 100 ml-flask equipped with a stirrer and a thermometer were added the diamine component and n-methyl-2-pyrrolidone as indicated in Table 2, and dissolved with stirring at ambient temperature. To the solution was added the acid component as indicated in Table 2, and stirred for 30 hours to give a viscous solution of a polyimide precursor.

The solutions were heated at 70° C. for 5 hours to adjust their viscosities to 80 poise (solid content: 25 wt %), to obtain solutions of polyimide precursors PA-1, PA-2, PA-4 and PA-5. Table 2 also indicates the amounts of the diamine components, acid components and N-methyl-2-pyrrolidone (NMP). The polyimide precursors PA-1 and PA-2 respectively had repetitive units of the following structures.

(PA-1)

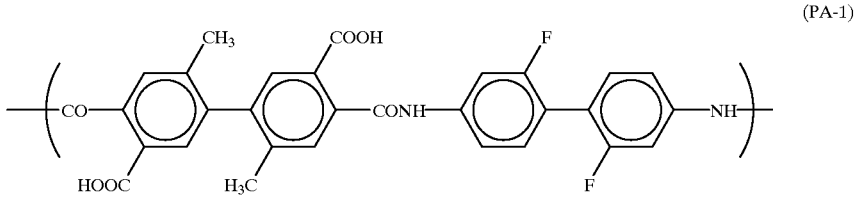

-continued (PA-2)

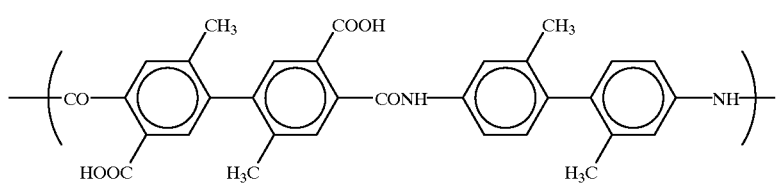

Synthetic Example 3

(1) Synthesis of an Acyl Chloride

To a 4-necked 200 ml flask were added 0.03 mol of the acid anhydride as indicated in Table 2, 7.81 g (0.06 mol) of 2-hydroxyethyl methacrylate (HEMA), 4.75 g (0.06 mol) of pyridine, 0.01 g of hydroquinone and 70 ml of N,N-dimethylacetamide. When stirred at 60° C., the mixture became a clear solution in 2 hours. After stirring the solution for 7 hours at ambient temperature, the flask was cooled with ice, and 8.57 g (0.072 mol) of thionyl chloride was added dropwise thereto over a period of 10 minutes. The mixture was stirred at ambient temperature for 1 hour, to obtain a solution containing a tetracarboxylic acid diester dichloride of the following structure.

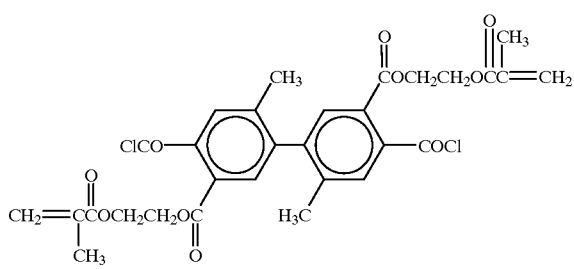

(2) Synthesis of a Polyimide Precursor

To another 4-necked 200 ml flask were added 0.03 mol of the diamine as indicated in Table 2, 5.06 g (0.064 mol) of pyridine, 0.01 g of hydroquinone and 50 ml of DMAc. While ice-cooling the flask to keep the temperature of the mixture at 10° C. or lower with stirring, the solution of the tetracarboxylic diester dichloride obtained by the above synthesis (1) was slowly added dropwise over a period of 1 hour. Subsequently, the mixture was stirred for 1 hour at ambient temperature, and poured into one liter of water to precipitate a polymer. The polymer was separated by filtration, washed twice, and dried under vacuum.

The powdery polymer was dissolved in γ-butyrolactone (γ-BL) to adjust the viscosity to 80 poise, to obtain a solution of a polyimide precursor (PA-3) having repetitive units of the following structure.

(PA-3)

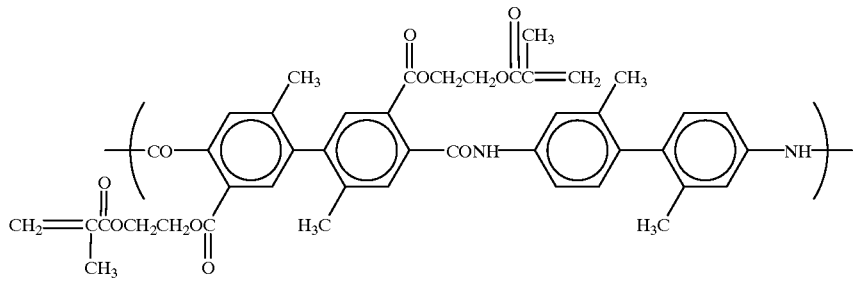

Measurements of viscosity were carried out by using an E-type viscometer (Model EHD, produced by Toki Sangyo Co., Ltd.) at a temperature of 25° C. at a rotation number of 2.5 rpm.

The solutions (PA-1 to PA-5) of polyimide precursors were dried and subjected to measurement of an infrared absorption spectrum by a KBr method (Model JIR-100 produced by Japan Electron Co., Ltd.). All spectra indicated an absorption due to C=O of amido groups in the vicinity of 1600 cm$^{-1}$ and an absorption due to N—H in the vicinity of 3300 cm$^{-1}$

TABLE 2

| | Acid/ Amount | Diamine/ Amount | Solvent/ Amount | Polyimide precursor |
|---|---|---|---|---|
| Synthetic example 1 | MBDA/ 32.23 g (0.1 mol) | DFAP/ 22.02 g (0.1 mol) | NMP/ 162.75 g | PA-1 |
| Synthetic example 2 | MBDA/ 32.23 g (0.1 mol) | DMAP/ 21.23 g (0.1 mol) | NMP/ 160.38 g | PA-2 |
| Synthetic example 3 | MBDA(HEMA)/ 32.23 g (0.1 mol) | DMAP/ 21.23 g (0.1 mol) | γ-BL/ 160.38 g | PA-3 |
| Synthetic example 4 | s-BPDA/ 29.42 g (0.1 mol) | DMAP/ 21.23 g (0.1 mol) | NMP/ 151.95 g | PA-4 |
| Synthetic example 5 | ODPA/ 31.02 g (0.1 mol) | DMAP/ 21.23 g (0.1 mol) | NMP/ 156.75 g | PA-5 |

MBDA: 6,6'-dimethyl-3,3',4,4'-biphenyltetracarboxylic dianhydride
ODPA: 4,4'-oxydiphthalic dianhydride
s-BPDA: biphenyltetracarboxylic dianhydride
DFAP: 2,2'-difluro-4,4'-diaminobiphenyl
DMAP: 2,2'-dimethyl-4,4'-diaminobiphenyl
HEMA: 2-hydroxyethyl methacrylate

Examples 4 and 5 and Comparative Examples 3 and 4

Negative, photosensitive resin compositions to be used in Examples 4 and 5 and Comparative Examples 3 and 4 were prepared as follows by using the polyimide precursors (PA-1, PA-2, PA-4 and PA-5) respectively. To 10 g of each polyimide precursor solution were added 0.027 g of 2,6-bis (4'-azidobenzal)-4-carboxycyclohexanone (CA), 0.027 g of 4,4'-bis(diethylamino)benzophenone (EAB) and 0.054 g of 1-phenyl-2-(o-ethoxycarbonyl)oxyiminopropane-1-one (PDO), and to the mixture was added dimethylaminopropyl methacrylate in an equivalent amount to carboxyl groups of the polyimide precursor. The mixture was stirred to obtain a uniform, negative, photosensitive resin composition.

Each negative, photosensitive resin composition was filtered, and dropped to apply it onto a silicon wafer by spin coating.

The applied composition was heated on the wafer using a hot plate at 100° C. for 150 seconds to form a coating film of 23 μm, and exposed to i-line of 200 mJ/cm² with an i-line stepper through a patterned mask.

It was then heated at 100° C. for 60 seconds, developed with a solution mixture of N-methyl-2-pyrrolidone/water (75/25 in weight ratio) using a paddle, heated at 100° C. for 30 minutes, at 200° C. for 30 minutes, and at 350° C. for 60 minutes, to obtain a relief pattern of a polyimide having the following repetitive units.

Example 4

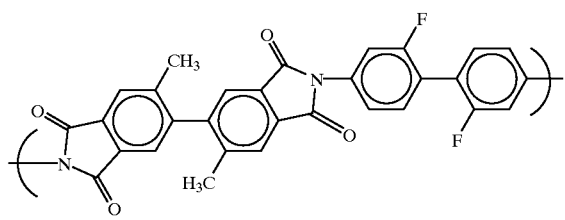

Example 5

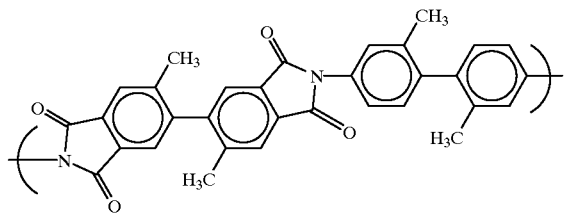

An infrared absorption spectrum of a part of each polyimide relief pattern as measured by a KBr method indicated an absorption due to imido in the vicinity of 1780 cm⁻¹.

Example 6

10 g of the polyimide precursor (PA-3) obtained in Synthetic example 3 was dissolved in 15 g of γ-butyrolactone (γ-BL), and to the mixture were added 100 mg of Michler's ketone and 200 mg of 1,3-diphenyl-1,2,3-propanetrione-2-(o-ethoxycarbonyl)oxime and dissolved therein, to give a uniform, photosensitive resin composition to be used in this Example.

The photosensitive resin composition was filtered, and dropped to apply it onto a silicon wafer by spin coating.

The applied composition was heated on the wafer using a hot plate to 100° C. for 150 seconds to form a coating film of 23 μm, and exposed to i-line of 200 mJ/cm² with an i-line stepper through a patterned mask.

It was developed with a solution mixture of N-methyl-2-pyrrolidone/cyclopentane (70/30 in weight ratio) using a paddle, heated at 100° C. for 30 minutes and at 350° C. for 60 minutes, to obtain a relief pattern of a polyimide having the following repetitive units.

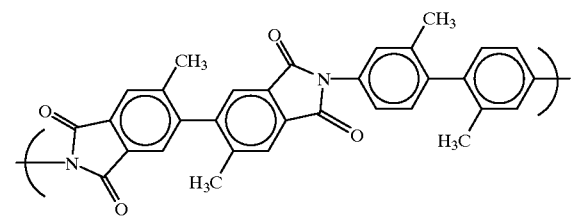

An infrared absorption spectrum of a part of the polyimide relief pattern as measured by a KBr method indicated an absorption due to imido in the vicinity of 1780 cm⁻¹.

By the following methods were evaluated the 1-line percent transmittances of the polyimide precursors (PA-1 to PA-5) used in Examples 4, 5 and 6 and Comparative Examples 3 and 4, the glass transition temperatures of the polyimide films formed as described above, and the resolutions of the relief patterns on silicon wafers. The results are indicated in Table 3.

The measurement of i-line percent transmittance was conducted with a spectrophotometer on a 20 μm coating film formed by spin-coating each of the polyimide precursor solutions (PA-1 to PA-5), and drying it at 85° C. for 3 minutes and at 105° C. for 3 minutes.

The measurement of glass transition temperature was conducted on 10 μm thick polyimide films with a TMA at a heating rate of 10° C./min under a load of 10 g.

A through hole-testing pattern was used to evaluate resolution by the size of the smallest through hole that could be developed.

Subsequently, the relief patterns formed in Examples 4, 5 and 6 and Comparative Examples 3 and 4 were heated at 100° C. for 30 minutes, at 200° C. for 30 minutes, and then under nitrogen at 400° C. for 60 minutes, to obtain polyimide patterns. The polyimide patterns formed from the relief patterns of Examples 4, 5 and 6 were of good profiles, reflecting their good resolutions, while the polyimide patterns formed from the relief patterns of Comparative Examples 3 and 4 were of defective profiles, reflecting their low resolutions.

TABLE 3

| | Polyimide precursor | Percent transmittance (%) | Resolution | Glass transition temperature (° C.) |
|---|---|---|---|---|
| Example 4 | PA-1 | 56 | 3 μ□ | 400 |
| Example 5 | PA-2 | 55 | 3 μ□ | 380 |
| Example 6 | PA-3 | 56 | 3 μ□ | 380 |
| Comp. example 3 | PA-4 | 5 | 8 μ□ | 370 |
| Comp. example 4 | PA-5 | 56 | 5 μ□ | 290 |

Positive, Photosensitive Resin Compositions

Example 7

To a 0.5-liter flask equipped with a stirrer, a thermometer and a Dimroth condenser were added 25.78 g of 6,6'-dimethyl-3,3',4,4'-biphenyltetracarboxylic dianhydride and 59.30 g of n-butyl alcohol, and stirred at 95° C. for 5 hours to conduct reaction. Excess n-butyl alcohol was distilled away under reduced pressure, to obtain 6,6'-dimethyl-3,3',4,4'-biphenyltetracarboxylic acid di-n-butyl ester. To the flask were added 95.17 g of thionyl chloride and 70.00 g of toluene, and reaction was conducted at 40° C. for 3 hours. The pressure was reduced to remove excess thionyl chloride as a toluene azeotrope. To the flask was added 186 g of n-methylpyrrolidone, to obtain a solution (α) of 6,6'-dimethyl-3,3',4,4'-biphenyltetracarboxylic acid di-n-butyl ester dichloride. To a 0.5-liter flask equipped with a stirrer, a thermometer and a Dimroth condenser were added 95 g of N-methylpyrrolidone followed by 8.28 g of 3,5-diaminobenzoic acid and 5.13 g of 4,4'-diaminodiphenyl ether. After the mixture was dissolved with stirring, 12.66 g of pyridine was added thereto, and, while the temperature was kept at 0 to 5° C., the solution (α) of 6,6'-dimethyl-3,3',4,4'-biphenyltetracarboxylic acid di-n-butyl ester dichloride was dropped therein over a period of 1 hour, and the stirring was continued for 1 hour. The solution was poured into 4 liters of water, and the precipitate was collected, washed and vacuum dried, to obtain an n-butyl polyamidate (hereinafter referred to as Polymer I) having the following repetitive units.

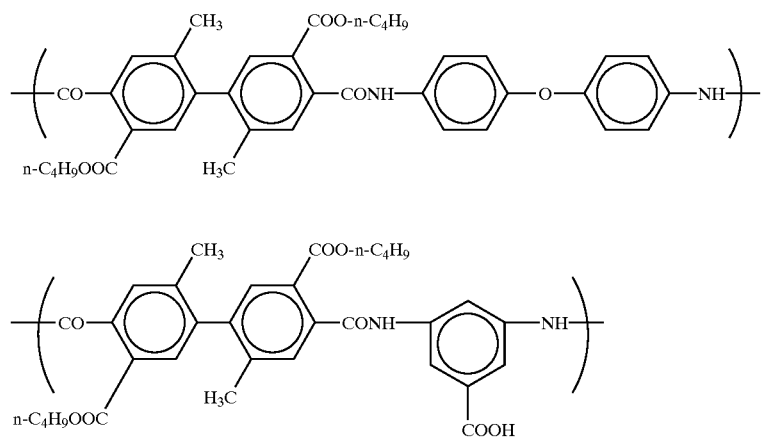

30 g of Polymer I was dissolved in 54 g of NMP with stirring. After the addition of 0.9 g of 3-isocyanatopropyltriethoxysilane, the stirring was continued for 12 hours. In the solution was dissolved 7.5 g of a compound X prepared by the reaction of 2,3,4,4'-tetrahydroxybenzophenone with 1,2-naphthoquinone-2-diazido-5-sulfonyl chloride in a molar ratio of 1/3. The resulting solution was filtered under increased pressure through a 3 μm-Teflon filter to obtain a positive, photosensitive resin composition.

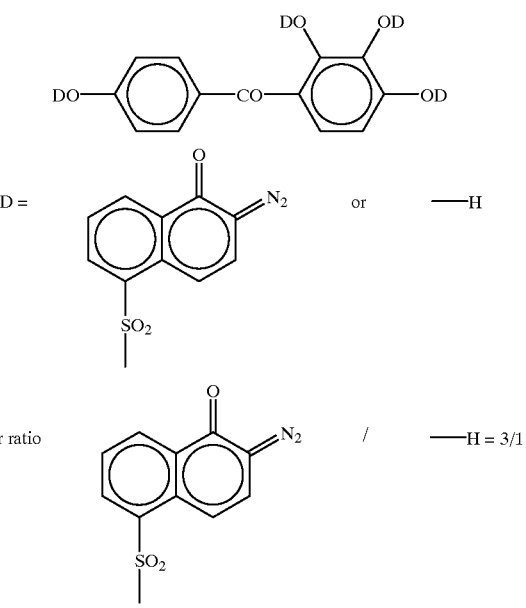

The positive, photosensitive resin composition was applied onto a silicon wafer by spin-coating using a spinner, and dried with heat on a hot plate at 125° C. for 3 minutes to form a 10.8 μm film of the positive, photosensitive resin composition. The coating film was exposed to i-line of 700 mJ/cm² through a mask with line/gap patterns of equivalent widths ranging from 3 to 100 μm, using an i-line reduction injection aligner (LD-5010i, produced by Hitachi, Ltd.). The exposed film was developed with a developer, a 2.38 wt % aqueous tetramethylammonium hydroxide solution, for 70 seconds, using a paddle, and rinsed with pure water to form a relief pattern. The developed relief was 8.5 μm thick. The smallest opening was 5 μm wide. The pattern was heated under nitrogen at 400° C. for 1 hour to obtain a polyimide film pattern of 5.6 μm thick having the following repetitive units.

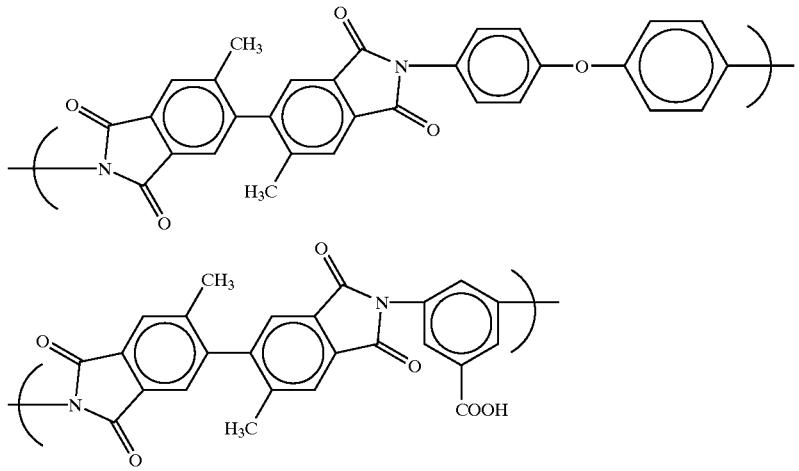

Example 8

To a 0.5-liter flask equipped with a stirrer, a thermometer and a Dimroth condenser were added 25.78 g of 6,6'-dimethyl-3,3',4,4'-biphenyltetracarboxylic dianhydride and 59.3 g of n-butyl alcohol, and stirred at 95° C. for 5 hours to conduct reaction. Excess n-butyl alcohol was removed by vacuum distillation to obtain 6,6'-dimethyl-3,3',4,4'-biphenyltetracarboxylic acid di-n-butyl ester. To the flask were added 95.17 g of thionyl chloride and 70.00 g of toluene, and reaction was conducted at 40° C. for 3 hours. The pressure was reduced to remove excess thionyl chloride as a toluene azeotrope. To the flask was added 186 g of n-methylpyrrolidone to obtain a solution (β) of 6,6'-dimethyl-3,3',4,4'-biphenyltetracarboxylic acid di-n-butyl ester dichloride. To a 0.5-liter flask equipped with a stirrer, a thermometer and a Dimroth condenser were added 95 g of N-methylpyrrolidone followed by 19.76 g of 2,2-bis(3-amino-4-hydroxyphenyl)hexafluoropropane and 5.13 g of 4,4'-diaminodiphenyl ether. After the mixture was dissolved with stirring, 12.66 g of pyridine was added thereto, and, while the temperature was kept at 0 to 5° C., the solution (γ) of 6,6'-dimethyl-3,3',4,4'-biphenyltetracarboxylic acid di-n-butyl ester dichloride was dropped therein over a period of 1 hour, and the stirring was continued for 1 hour. The solution was poured into 4-liter of water, and the precipitate was collected, washed and vacuum dried, to obtain an n-butyl polyamidate (hereinafter referred to as Polymer II) having the following repetitive units.

30 g of Polymer II was dissolved in 54 g of NMP with stirring. After addition of 0.12 g of 3-isocyanatopropyltriethoxysilane, the stirring was continued for 6 hours. In the solution was dissolved 6 g of a compound Y prepared by the reaction of tris(4-hydroxyphenyl)methane with 1,2-naphthoquinone-2-diazido-5-sulfonyl chloride in a molar ratio of 1/2.5. The resulting solution was filtered under increased pressure through a 3 μm-Teflon filter to obtain a positive, photosensitive resin composition.

Y:

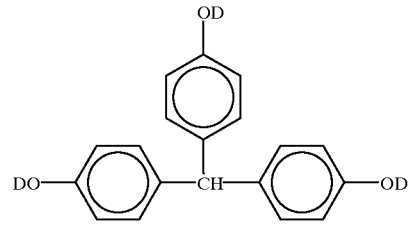

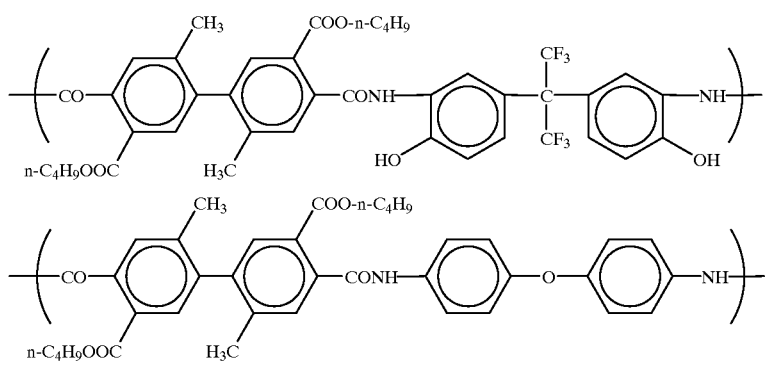

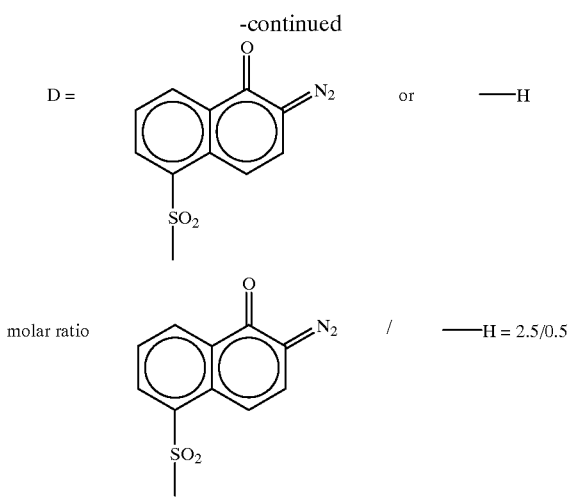

molar ratio = 2.5/0.5

The positive, photosensitive resin composition was applied onto a silicon wafer by spin-coating using a spinner, and dried with heat on a hot plate at 90° C. for 3 minutes to form a 10.4 μm film of the positive, photosensitive resin composition. The coating film was exposed to i-line of 600 mJ/cm² through a mask with line/gap patterns of equivalent widths ranging from 3 to 100 μm, using an i-line reduction injection aligner (LD-5010i, produced by Hitachi, Ltd.). The exposed film was developed with a developer, a 2.38 wt % aqueous tetramethylammonium hydroxide solution, for 60 seconds, using a paddle, and rinsed with pure water to form a relief pattern. The developed relief was 8.6 μm thick. The smallest opening was 5 μm wide. The pattern was heated under nitrogen at 400° C. for 1 hour to obtain a polyimide film pattern of 5.4 μm thick having the following repetitive units.

at 40° C. for 3 hours. The pressure was reduced to remove excess thionyl chloride as a toluene azeotrope. To the flask was added 186 g of n-methylpyrrolidone to obtain a solution (γ) of 4,4',5,5'-biphenyltetracarboxylic di-n-butyl ester dichloride. To a 0.5-liter flask equipped with a stirrer, a thermometer and a Dimroth condenser were added 95 g of N-methylpyrrolidone followed by 8.28 g of 3,5-diaminobenzoic acid and 5.13 g of 4,4'-diaminodiphenyl ether. After the mixture was dissolved with stirring, 12.66 g of pyridine was added thereto, and, while the temperature was kept at 0 to 5 C, the solution (γ) of 4,4',5,5'-biphenyltetracarboxylic di-n-butyl ester dichloride was dropped therein over a period of 1 hour, and the stirring was continued for 1 hour. The solution was poured into 4 liters of water, and the precipitate was collected, washed and vacuum dried, to obtain a n-butyl polyamidate (hereinafter referred to as Polymer III).

30 g of Polymer III was dissolved in 54 g of NMP with stirring. After addition of 0.9 g of 3-isocyanatopropyltriethoxysilane, stirring was continued for 12 hours. In the solution was dissolved 7.5 of a compound prepared by the reaction of 2,3,4,4'-tetrahydroxybenzophenone with 1,2-naphthoquinone-2-diazido-5-sulfonyl chloride in a molar ratio of 1/3. The resulting solution was filtered under increased pressure through a 3 Mm-Teflon filter to obtain a positive, photosensitive resin composition.

The positive, photosensitive resin composition was applied onto a silicon wafer by spin-coating using a spinner, and dried with heat on a hot plate at 125° C. for 3 minutes to form a 9.8 μm film of the positive, photosensitive resin composition. The coating film was exposed to i-line of 1000 mJ/cm² through a mask with line/gap patterns of equivalent widths ranging from 3 to 100 μm, using an i-line reduction injection aligner (LD-5010i, produced by Hitachi, Ltd.). The exposed film was developed with a developer, a 2.38 wt % aqueous tetramethylammonium hydroxide solution, for 90

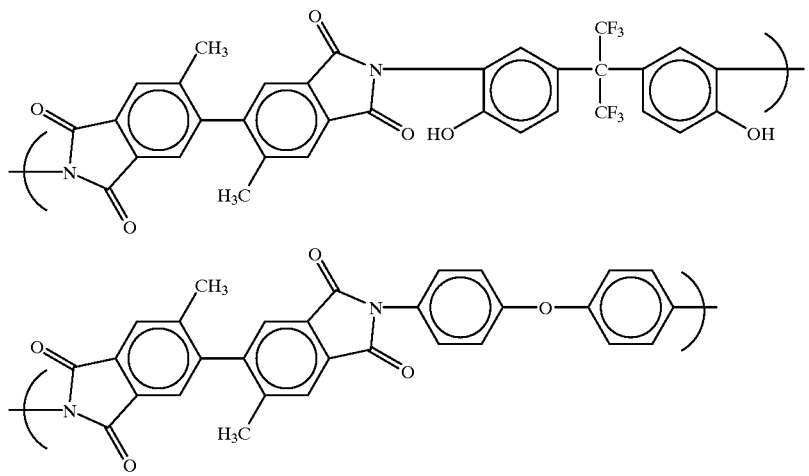

Comparative Example 5

To a 0.5-liter flask equipped with a stirrer, a thermometer and a Dimroth condenser were added 23.54 g of 4,4',5,5'-biphenyltetracarboxylic dianhydride and 59.30 g of n-butyl alcohol, and stirred at 95° C. for 5 hours to conduct reaction. Excess n-butyl alcohol was distilled away under reduced pressure to obtain 4,4',5,5'-biphenyltetracarboxylic di-n-butyl ester. To the flask were added 95.17 g of thionyl chloride and 70.00 g of toluene, and reaction was conducted seconds, using a paddle, and rinsed with pure water to form a relief pattern. The developed relief was 8.0 μm thick. The smallest opening was 20 μm wide. The pattern was heated under nitrogen at 400° C. for 1 hour to obtain a polyimide film pattern of 5.2 μm thick having the following repetitive units.

Examples 4 to 8 and Comparative Examples 3 to 5 show the excellence of the photosensitive resin compositions of the invention in sensitivity to i-line, shortened developing time and resolution of developed relief patterns. On the other hand, the photosensitive resin compositions of Comparative Examples 3 to 5 are inferior in the resolution of the developed relief patterns.

What is claimed is:

1. A method of preparing a 6,6'-dialkyl-3,3',4,4'-biphenyltetracarboxylic dianhydride, comprising brominating a 4-alkylphthalic anhydride at its 5-position, and then coupling the bromination product in the presence of a nickel catalyst.

2. The method of claim 1, which comprises heating a water suspension of a 4-alkylphthalic anhydride and a bromate and adding thereto concentrated sulfuric acid to form a 4-alkyl-5-bromophthalic acid, esterifying the 4-alkyl-5-bromophthalic acid to form a 4-alkyl-5-bromophthalic diester, coupling the 4-alkyl-5-bromophthalic diester in the presence of a nickel catalyst to form a 6,6'-dialkyl-3,3',4,4'-biphenyltetracarboxylic tetraester, hydrolyzing the 6,6'-dialkyl-3,3',4,4'-biphenyltetracarboxylic tetraester to form a 6,6'-dialkyl-3,3',4,4'-biphenyltetracarboxylic acid, and dehydrating the 6,6'-dialkyl-3,3',4,4'-biphenyltetracarboxylic acid into a 6,6'-dialkyl-3,3',4,4'-biphenyltetracarboxylic dianhydride.

* * * * *